US006762172B1

(12) United States Patent
Elfersy et al.

(10) Patent No.: US 6,762,172 B1
(45) Date of Patent: Jul. 13, 2004

(54) WATER-STABILIZED ORGANOSILANE COMPOUNDS AND METHODS FOR USING THE SAME

(75) Inventors: Jacques E. Elfersy, Atlanta, GA (US); Joachim Berkner, Smyrna, GA (US); Timothy C. Moses, Atlanta, GA (US)

(73) Assignees: Nova Biogenetics, Inc., Atlanta, GA (US); International Biochemical Industries, Inc., Norcross, GA (US)

( * ) Notice: Subject to any disclaimer, the term of this patent is extended or adjusted under 35 U.S.C. 154(b) by 0 days.

(21) Appl. No.: 09/967,486

(22) Filed: Sep. 28, 2001

Related U.S. Application Data

(63) Continuation of application No. 09/118,154, filed on Jul. 17, 1998, now abandoned.
(60) Provisional application No. 60/052,888, filed on Jul. 17, 1997.

(51) Int. Cl.$^7$ .......................... A01N 55/00; C07F 7/10; C07F 7/12; C07F 7/18

(52) U.S. Cl. ...................... 514/63; 424/405; 424/406; 528/34; 528/38; 556/413; 556/418; 556/419; 556/423; 556/424

(58) Field of Search ........................... 514/63; 556/413, 556/418, 419, 423, 224; 528/34, 38; 424/405, 406

(56) References Cited

U.S. PATENT DOCUMENTS

| | | | |
|---|---|---|---|
| 3,560,385 A | 2/1971 | Roth ......................... 252/49.6 |
| 3,730,701 A | 5/1973 | Isquith et al. .................. 71/67 |
| 3,794,736 A | 2/1974 | Abbott et al. ................. 424/78 |
| 3,814,739 A | 6/1974 | Takeda .................... 260/85.51 |
| 3,817,739 A | 6/1974 | Abbott et al. ................. 424/78 |
| 3,860,709 A | 1/1975 | Abbott et al. ............... 424/184 |
| 3,865,728 A | 2/1975 | Abbott et al. ............... 210/169 |
| 4,035,332 A | 7/1977 | Gomyo et al. ....... 260/33.2 SB |
| 4,110,263 A | 8/1978 | Lindermann et al. ....... 252/545 |
| 4,243,767 A | 1/1981 | Kaufmann et al. ......... 525/102 |
| 4,282,366 A | 8/1981 | Eudy .......................... 556/413 |
| 4,284,548 A | 8/1981 | Kaufmann et al. ........... 260/38 |
| 4,395,454 A | 7/1983 | Baldwin ..................... 428/290 |
| 4,408,996 A | 10/1983 | Baldwin ..................... 428/259 |
| 4,413,086 A | 11/1983 | Chang et al. ............... 524/386 |
| 4,414,268 A | 11/1983 | Baldwin ..................... 428/289 |
| 4,446,292 A | 5/1984 | Chang et al. ................. 528/29 |
| 4,465,849 A | 8/1984 | Terae et al. ................. 556/450 |
| 4,467,081 A | 8/1984 | Chang et al. ................. 528/26 |
| 4,501,872 A | 2/1985 | Chang et al. ................. 528/18 |
| 4,504,541 A | 3/1985 | Yasuda et al. .............. 428/264 |
| 4,514,342 A | 4/1985 | Billington et al. .......... 260/952 |
| 4,555,545 A | 11/1985 | Kimura et al. .............. 524/858 |
| 4,561,435 A | 12/1985 | McKnight et al. .......... 128/156 |
| 4,613,451 A | 9/1986 | Chang et al. ............... 252/182 |
| 4,615,882 A | 10/1986 | Stockel ........................ 424/80 |
| 4,615,937 A | 10/1986 | Bouchette .................. 428/288 |
| 4,622,369 A | 11/1986 | Chang et al. ............... 525/440 |
| 4,623,697 A | 11/1986 | Chang et al. ................. 525/61 |
| 4,631,273 A | 12/1986 | Blehm et al. ................ 514/29 |
| 4,657,941 A | 4/1987 | Blackwell et al. ........... 522/14 |
| 4,692,374 A | 9/1987 | Bouchette .................. 428/288 |
| 4,736,467 A | 4/1988 | Schwartz et al. .............. 2/114 |
| 4,772,593 A | 9/1988 | Whalen et al. ............... 514/63 |
| 4,822,667 A | 4/1989 | Goad et al. ................. 428/265 |
| 4,919,998 A | 4/1990 | Goad et al. ................. 428/265 |
| 4,939,289 A | 7/1990 | Oxenrider et al. ............ 560/87 |
| 5,024,851 A | 6/1991 | Goad et al. ..................... 427/2 |
| 5,027,438 A | 7/1991 | Schwartz et al. .............. 2/114 |
| 5,035,892 A | 7/1991 | Blank et al. ................. 424/443 |
| 5,064,613 A | 11/1991 | Higgs et al. .................. 422/16 |
| 5,073,298 A | 12/1991 | Gentle et al. ............... 252/358 |
| 5,135,811 A | 8/1992 | White et al. ................ 428/395 |
| 5,174,813 A | 12/1992 | Cifuentes et al. .............. 106/3 |
| 5,244,718 A | 9/1993 | Taylor et al. ............... 428/229 |
| 5,389,364 A | 2/1995 | Cifuentes et al. ...... 424/70.122 |
| 5,411,585 A | 5/1995 | Avery et al. ............. 106/278.1 |
| 5,959,014 A | 9/1999 | Liebeskind et al. ......... 524/389 |

FOREIGN PATENT DOCUMENTS

WO      9826028      12/1997

OTHER PUBLICATIONS

S. F. Hayes and W. C. White, "How Antimicrobial Treatment Can Improve Nonwovens," Reprinted from the *American Dyestuff Reporter* (1984).

R. L. Gettings and B. L. Triplett, "A New, Durable Antimicrobial Finish for Textiles," Reprinted from the 1978 *Book of Paper*, pp 259–261, 1978 American Association of Textile Chemists and Colorists National Technical Conference.

P. A. Walters, E. A. Abbott and A. J. Isquith, "Algicidal Activity of a Surface–Bonded Organosilicon Quatemary Ammonium Chloride," *Applied Microbiology*, 25:253–256 (1973).

J. B. McGee, J. R. Malek and W. C. White, "New Antimicrobial Treatment for Carpet Applications," Reprinted from the Jun. 1983 issue of *American Dyestuff Reporter* by Dow Corning Corp.

(List continued on next page.)

*Primary Examiner*—Peter O'Sullivan
(74) *Attorney, Agent, or Firm*—Saliwanchik, Lloyd & Saliwanchik

(57) ABSTRACT

The composition formed by mixing an organosilane with an organic carbonate. Water-stabilized organosilane compounds. A water stable composition made from the organic carbonate and organosilane composition and water. A method of treating a substrate by mixing or contacting the substrate with the product, compound, or composition of this invention for a period of time sufficient for treatment of the substrate. A treated substrate having adhered thereto the product, compound, or composition of this invention. A method of dyeing and treating a substrate. A method of antimicrobially treating a food article. A method of antimicrobially coating a fluid container. A method of antimicrobially coating a latex medical article.

22 Claims, No Drawings

OTHER PUBLICATIONS

A. J. Isquith, E. A. Abbott and P. A. Walters, "Surface–Bonded Antimicrobial Activity of an Organosilicon Quaternary Ammonium Chloride," *Applied Microbiology* 24:859–863 (1972).

W. D. Hanrahan and A. S. Patil, "Fighting Bacteria from Within," *Textile Technology International*, pp 173–175 (1996).

M. Gruender, "New Acetate Works Against Bacteria," *F. W.:Fiber Technology* (Jan. 1996).

Chemical Abstracts 85:125721x (1976).

Chemical Abstracts 83:207489a (1975).

Chemical Abstracts 98:909936b (1983).

WATER-STABILIZED ORGANOSILANE COMPOUNDS AND METHODS FOR USING THE SAME

CROSS-REFERENCE TO A RELATED APPLICATION

This is a continuation of application Ser. No. 09/118,154, filed Jul. 17, 1998, now abandoned, and claims the benefit of provisional application No. 60/052,888, filed Jul. 17, 1997, which is incorporated herein by reference.

BACKGROUND OF THE INVENTION

1. Field of the Invention

The invention relates to organosilane compounds, products and methods for their use. In particular, this invention provides water-stable organosilane compounds, products, and compositions for treating various substrates; articles treated with the compounds, products and compositions; and methods of treatment using the compounds, products and compositions.

2. Background

Organosilanes of the general formula $R_nSiX_{4-n}$ where n is an integer of from 0 to 3, but more generally from 0 to 2 (where when n is 3 the organosilanes may only dimerize); R is a nonhydrolyzable organic group, such as, but not limited to, alkyl, aromatic, organofunctional, or a combination thereof, and X is alkoxy, such as methoxy or ethoxy, are prone to self-condensation rendering such organosilanes unstable in water over commercially relevant periods of time. Additionally, X can be a halogen, such as Cl, Br, or I, and is similarly liberated as HCl, HBr, or HI. For such organosilanes, the X moiety reacts with various hydroxyl containing molecules in aqueous media to liberate methanol, ethanol, HCl, HBr, HI, $H_2O$, acetic acid, or an unsubstituted or substituted carboxylic acid and to form the hydroxylated, but condensation-prone compound.

For organosilanes $R_nSiX_{4-n}$, where n is an integer from 0 to 2, hydrolysis of the first two X groups with water produces a species bearing —$Si(OH)_2$— units which can self-condense through the hydroxyl moieties to linear and/or cyclic oligomers possessing the partial structure HO—Si—(O—Si)$_{mm}$—O—Si—O—Si—O—Si—OH, where mm is an integer such that an oligomer is formed. For those cases, $RSiX_3$, hydrolysis of the third X group generates a silanetriol $(RSi(OH)_3)$ which produces insoluble organosilicon polymers through linear and/or cyclic self-condensation of the Si(OH) units. This water induced self-condensation generally precludes storage of most organosilanes $R_nSiX_{4-n}$, where n ranges from 0 to 2, inclusive, in water. Except for some organosilanes which can be stable in very dilute solutions at specific pH ranges, the use of water solutions of most organosilanes require the use of freshly prepared solutions.

One commercially relevant example of an organosilane suffering from such undesirable self-condensation is the antimicrobial Dow Corning 5700 (Dow Corning Corporation, Midland, Mich.). The literature describes the active ingredient of Dow Corning 5700 as 3-(trimethoxysilyl)propyl-dimethyloctadecyl ammonium chloride. However, in aqueous media, it is believed that the correct active ingredient is more likely 3-(trihydroxysilyl)propyl-dimethyloctadecyl ammonium chloride. Nonetheless, Dow Corning 5700 is a water activated antimicrobial integrated system which is capable of binding to a wide variety of natural and synthetic substrates, including fibers and fabrics, to produce a durable surface or fabric coating. 3-(Trimethoxysilyl)propyl-dimethyloctadecyl ammonium chloride is prepared by quaternization of dimethyloctadecylamine with 3-chloropropyl trimethoxysilane.

The $C_{18}$ hydrocarbon chain quaternary ammonium portion of the molecule possesses long-acting antimicrobial properties and provides initial association with the surface of the substrate through ionic bonds and/or electrostatic interaction. Preferably, the treated surface becomes permanently coated with a covalently bound octadecylammonium ion, providing a durable, long-acting antimicrobial coating that is able to destroy microbes that come into contact with the surface.

Unfortunately, as noted above, organosilanes in water, such as the activated mixture of 3-(trimethoxysilyl)propyl-dimethyloctadecyl ammonium chloride and water, are generally unstable and prone to self-condensation. For instance, the mixture of 3-(trimethoxysilyl)propyl-dimethyloctadecyl ammonium chloride and water begins to lose effectiveness in as little as four to eight hours. Gel formation in this and similar silane formulations in water begins to occur in even shorter times. The limitations of such organosilanes in aqueous media are further described in U.S. Pat. No. 5,411,585, the contents of which are hereby incorporated by this reference. Moreover, such products are notorious for agitation difficulty during the addition of the silane to water.

The use of quaternary ammonium silicon compounds as antimicrobial agents in accordance with the prior art is well known and taught in a wide variety of U.S. Pat. Nos., e.g., 3,560,385; 3,794,736; 3,814,739, the contents of which are hereby incorporated by this reference. It is also taught that these compounds possess certain antimicrobial properties which make them valuable and very useful for a variety of surfaces, substrates, instruments and applications (see, e.g., U.S. Pat. Nos. 3,730,701; 3,794,736; 3,860,709; 4,282,366; 4,504,541; 4,615,937; 4,692,374; 4,408,996; and 4,414,268, the contents of which are hereby incorporated by this reference). While these quaternary ammonium silicon compounds have been employed to sterilize or disinfect many surfaces, their employment is still limited because of their toxicity often as a result of the solvent system used to deliver the compound, the necessity for a solvent solution (for instance, Dow Corning antimicrobial agent 5700 contains over 49% methanol), short term stability (stability of aqueous silane solutions varies from hours to several weeks only), and poor water solubility. For instance, while 3-(trimethoxysilyl)propyl-dimethyloctadecyl ammonium chloride does not suffer from water insolubility, it is difficult to dissolve in water and tends to form lumps before it slowly dissolves. It is unstable in water, and, because it is shipped in 50% methanol, it is overly toxic and flammable. Many other antimicrobial organosilanes, especially quaternary ammonium silicon compounds, also suffer from problems associated with physical health hazards, e.g., precautions must be taken to avoid contact with both skin and eyes, accidental spills to the surrounding area, flammability, and the added manufacturing steps needed in order to incorporate the such antimicrobial agents into other articles and surfaces, resulting in much higher manufacturing costs.

Therefore, there exists a need for extended shelf-life, water-stable organosilane compounds, products and compositions whereby, upon application, the active portion of the organosilane is operative for the selected application. Moreover, there exists a need for water-stable, organosilane compounds, products and compositions which are essentially non-toxic, non-flammable, uniformly dispersable, and simple and economical to use.

There also exists a need for highly concentrated organosilane compositions which are essentially non-toxic or of low toxicity, non-flammable, uniformly dispersable and simple and economical to use and stable in water when further diluted with water.

In the instant application we disclose the finding that compounds having at least one carbonate group stabilize aqueous organosilane solutions. The archetypal example of carbonates useful according to the instant invention is propylene carbonate.

BRIEF SUMMARY OF THE INVENTION

The present invention fulfills these needs by providing water-stable organosilane compounds, products (i.e., the compounds or compositions formed from performing a specified reaction) and compositions, methods for their use, and articles prepared using the compounds, products, and compositions.

In particular, the present invention provides the product formed from mixing an organosilane of the formula $R_nSiX_{4-n}$ where n is an integer of from 0 to 3, preferably 0 to 2; each R is, independently, a nonhydrolyzable organic group; and each X is, independently, a hydrolyzable group (hereinafter, "organosilane of interest"); with an organic carbonate, preferably propylene carbonate.

Accordingly, in one embodiment, this invention provides a water-stable composition, comprising the product or composition of the invention and water.

In a further embodiment, the present invention provides a composition for treating a substrate, comprising a carrier and an effective amount of the product or compound of the invention.

In yet another embodiment, the present invention provides a method of treating a substrate, comprising mixing the substrate with a sufficient amount of the product, compound, or composition of the invention for a period of time sufficient for treatment of the substrate.

In a further embodiment, the present invention provides a composition for treating a substrate by incorporation in the substrate.

In a further embodiment, the present invention provides a composition for treating a substrate by incorporation into a polymer backbone.

In a further embodiment, the present invention provides a composition as a concentrated solution, easily diluted with water, providing a water stable composition.

In a further embodiment, the present invention provides a composition as a concentrated solution which is the product of the synthesis of the compounds it comprises.

In a further embodiment, the present invention provides a treated substrate having adhered thereto or dispersed therein the product, compound, or composition of the invention.

In addition, the present invention provides a method of dyeing and treating a substrate, comprising contacting the substrate with an aqueous composition comprising an aqueous soluble dye suitable for dyeing a substrate and the product formed from mixing an organosilane of interest with an organic carbonate.

A further embodiment of the present invention provides a method of antimicrobially treating a substrate selected from the group consisting of a concrete pipe, a tooth brush, a food article, fluid container, latex medical article, gloves, shoes, a comb, a hair brush, a denture, an orthodontic retainer, a spa or pool filter, an air filter, an HVAC air system, a cabin air system, a marble article, a statue, an exposed work of art, a PE, PP or polyester plastic cover, a silicone or TEFLON® coated fiberglass article, a Dryvitt finish, a stucco finish, blended cotton, a bio-film, a bio-adhesive, a single ply roofing, a roofing shingle, and a fiberglass reinforcement product, comprising contacting the substrate with an effective amount of the product formed from mixing an antimicrobial organosilane of interest with an organic carbonate.

In addition, the present invention also provides a method of antimicrobially enhancing a product of rubbing alcohol, a flower preservative, or a waterproofing solution, comprising admixing with the product an effective amount of the product formed from mixing an antimicrobial organosilane of interest with an organic carbonate.

A further embodiment of this invention is a method for making an organosilane of interest from starting materials in an aqueous solution in the presence of an organic carbonate.

Additional advantages of the invention will be set forth in part in the description which follows, and in part will be obvious from the description, or may be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

DETAILED DISCLOSURE OF THE INVENTION

The present invention may be understood more readily by reference to the following detailed description of preferred embodiments of the invention.

Before the present compounds, products, compositions, and methods are disclosed and described, it is to be understood that the terminology used herein is for the purpose of describing particular embodiments only and is not intended to be limiting. It is also to be understood that subject matter covered under the definition of certain terms, may, in some instances, fall under another term as well. It must be noted that, as used in the specification and the appended claims, the singular forms "a," "an" and "the" include plural referents unless the context clearly dictates otherwise.

Throughout this application, where publications are referenced, the disclosures of these publications in their entireties are hereby incorporated by reference into this application.

The term "alkyl" as used herein refers to a branched or unbranched saturated hydrocarbon group of 1 to 24 carbon atoms, such as methyl ("Me"), ethyl ("Et"), n-propyl, isopropyl, n-butyl, isobutyl, t-butyl, octyl, decyl, tetradecyl, hexadecyl, eicosyl, tetracosyl, and the like.

"Alkyl alcohol" as used herein refers to an alkyl having attached thereto one or more hydroxy moieties, such as, but not limited to, $-CH_2CH_2OH$, $CH_2CH(OH)CH_3$, $CH_2OH$, $CH_2CH_2CH_2OH$, $CH_2CH_2CH(OH)CH_3$, $CH_2CH_2CH(OH)CH_2OH$, or $CH_2CH(OH)CH(OH)CH_3$.

The term "alkoxy" as used herein intends an alkyl group bound through a single terminal ether linkage; that is, an "alkoxy" group may be defined as $-OR$ where R is alkyl as defined above.

"Glycol" as used herein refers to glycol compounds, which includes, but is not limited to, ethylene glycol, propylene glycol, butylene glycol, isobutylene glycol or hexylene glycol.

"Polyglycor" as used herein refers to a compound or moiety which takes the polymeric form of glycol, such as, but not limited to, polyethylene glycol or poly propylene glycol. Polyglycol would also include, for example, block and copolymers of ethylene glycol and propylene glycol. Polyglycols useful in the subject invention may have an average molecular weight of up to about 10,000 g/mol.

"Polyalkylethers" refers to alkyls or alkyl alchohols interconnected by or otherwise possessing multiple ether linkages. Polyalkylethers useful in the subject invention may have an average molecular weight of up to about 10,000 g/mol.

"Alkyl glycol" as used herein refers to an alkyl connected to a glycol through an ether linkage. An example of an alkyl glycol includes, but is not limited to, butyl glycol.

"Alkyl polyglycol" as used herein refers to alkyl connected to a polyglycol through and ether linkage. Alkyl polyglycol compounds useful in the subject invention may have an average molecular weight of up to 10,000 g/mol.

As used herein, "optional" or "optionally" means that the subsequently described event or circumstance may or may not occur, and that the description includes instances where said event or circumstance occurs and instances where it does not. For example, the phrase "optionally substituted lower alkyl" means that the lower alkyl group may or may not be substituted and that the description includes both unsubstituted lower alkyls and lower alkyls where there is substitution.

By the term "effective amount" of a compound, product, or composition as provided herein is meant a sufficient amount of the compound, product, or composition to provide the desired result. As will be pointed out below, the exact amount required will vary from substrate to substrate, depending on the particular compound, product, or composition used, its mode of administration, and the like. Thus, it is not always practical to specify an exact "effective amount," especially because a range of amounts or concentrations will usually be effective. However, an appropriate effective amount may be determined by one of ordinary skill in the art using only routine experimentation as a matter of optimization.

The term "cyclic" is used to refer to all aliphatic or aromatic hydrocarbons having one or more closed rings, whether unsaturated or saturated. Preferably, cyclic compounds possess rings of from 5 to 7 atoms, preferably 6 carbon atoms. Such rings fall into three classes: alicyclic, aromatic ("arene"), and heterocyclic. Moreover, when used with respect to cyclic compounds or moieties, the term "unsaturated" refers to such compound or moiety possessing at least one double or triple bond or otherwise constituting an aromatic compound or moiety. Moreover, the term "saturated" refers to compounds or moieties possessing no double or triple bonds within the ring, i.e., where all available valence bonds of an atom, especially carbon, are attached to other atoms.

The term "heterocyclic" refers to a cyclic compound or moiety where one or more of the carbon atoms of the ring has been substituted with a heteroatom, including, but not limited to O, N, or S.

The term "aryl" and "aromatic" are used interchangeably herein and refer to a compound or moiety whose molecules have a ring or multiple (poly) ring structure characteristic of benzene, naphthalene, phenanthrene, anthracene, etc. Examples of aryls or aromatics also include, but are not limited to, phenyl, benzyl, naphthyl, benzylidine, xylil, styrene, styryl, phenethyl, phenylene, benzenetrlyl, etc.

The term "heteroaryl" and "heteroaromatic" are used interchangebly and refer to an aryl where one or more of the carbon atoms of a ring have been substituted with a heteroatom, including, but not limited to, O, N, or S.

The term "cyclic alcohol" as used herein refers to a cyclic molecule substituted with one or more hydroxy moieties. Examples include, but are not limited to, Phenol and cyclohexanol.

As used herein, especially in reference to alkyl and alkoxy, the term "lower" refers to a moiety having from 1 to 6 carbon atoms, preferably 1 to 4 carbon atoms.

As used herein, the term "suitable" is used to refer a moiety which is compatible with the compounds, products, or compositions as provided herein for the stated purpose. Suitability for the stated purpose may be determined by one of ordinary skill in the art using only routine experimentation.

As used herein, "substituted" is used to refer, generally, to a carbon or suitable heteroatom having a hydrogen or other atom removed and replaced with a further moiety. In one embodiment, halogen, hydroxy, and nitrogen based substitutions of hydrocarbon hydrogens are contemplated as within the scope of the present invention for the claimed structures. Moreover, it is intended that "substituted" refers to substitutions which do not change the basic and novel utility of the underlying compounds, products, or compositions of the present invention. "Unsubstituted" refers to a structure wherein the reference atom does not have any further moieties attached thereto or substituted therefor.

As used herein, "branched" is used to refer, generally, to a moiety having a carbon chain backbone, e.g., alkyl or alkoxy, wherein the backbone may contain one or more subordinate carbon chain branches. For example, isobutyl, t-butyl, isopropyl, $CH_2CH_2C(CH_3)(H)CH_2CH_3$, $CH_2C(CH_2CH_3)(H)CH_2CH_3$, $CH_2CH_2C(CH_3)CH_3$, and $CH_2CH_2C(CH_3)_3$ would all be considered branched moieties. Moreover, it is intended that "branched" variations of the moieties herein described refer to variations which do not change the basic and novel utility of the underlying compounds, products, or compositions of the present invention. "Unbranched" refers to a structure wherein the carbon chain does not have any branches thereon, i.e., where the carbon chain extends in a direct line.

As used herein, the term "acyl" refers to organic acid derived moieties of the formula RCO where R is an organic molecule. The free valance on C is used to bond to other groups or atoms.

As used herein, the term "acyloxy" refers to organic acid derived moieties of the formula RCOX where R is an organic molecule and X, instead of being hydroxy, represents oxygen attached to another group or atom.

As used herein, the term "perfluoro" or "perfluoro-analog" refers to a hydrocarbon where the hydrogen atoms attached to carbons have been replaced with F atoms. Preferably, but not necessarily, in perfluoro-analogs, most if not all of the H atoms are replaced with F atoms. A "fluoro-" analog is contemplated to indicate a hydrocarbon where at least one hydrogen atom attached to a carbon is replaced with an F atom.

As used herein, "substrate" refers to any article, product, or surface that can be treated with the inventive compounds, preferably as enumerated hereinbelow under the heading "Uses," as described in the Examples hereto, and as specified in the relevant claims appended hereto. Suitable substrates are generally characterized by either having a negatively charged surface of oxygen atoms, or any surface capable of electrostatically, ionically, or covalently adhering or binding to the compounds, products, or compositions of the present invention. Preferably the adhering or binding occurs at the silicon atoms of the organosilane portion of the compounds, products, or compositions of the present invention, but such binding is not a requirement. "Substrate" also refers to materials that are treated by incorporation of the compounds and/or compositions of the present invention. Incorporation in this case includes the process of blending and mixing, and incorporation by becoming part of the material, i.e., polymer backbone and cement. As used herein, the term "adhere" is meant to refer to ionic, covalent, electrostatic, or other chemical attachment of a compound, product, or composition to a substrate.

As used herein, the term "antimicrobially enhancing" refers to the use of the compounds, products, or compositions of the present invention, preferably those wherein the organosilane has antimicrobial activity, along with other ingredients, surfactants, fillers, wetting agents, pigments, dyes, antimigrants, etc., to create a composition or solution capable of fulfilling its original purpose, based upon the other ingredients, and also of providing antimicrobial protection during the particular application. The term "enhance" refers to the addition of antimicrobial activity to such compositions or solutions where no such activity previously existed, or to the increase of antimicrobial activity where the starting compositions or solutions already possessed antimicrobial activity.

As used herein, "hydrolyzable" refers to whether the moiety is capable of or prone to hydrolysis (i.e., splitting of the molecule or moiety into two or more new molecules or moieties) in aqueous or other suitable media. Conversely, "nonhydrolyzable" refers to moieties that are not prone to or capable of hydrolysis in aqueous or other suitable media.

As used herein, "cationic" is used to refer to any compound, ion, or moiety possessing a positive charge. Moreover, "anionic" is used to refer to any compound, ion, or moiety possessing a negative charge. Furthermore, "monovalent" and "divalent" are used to refer to moieties having valances of one and two, respectively. As used herein, the term "salt" is meant to apply in its generally defined sense as "compound formed by replacing all or part of the hydrogen ions of an acid with one or more cations of a base." See, e.g., American Heritage Dictionary, Definition of "Salt" (1981). Therefore, suitable salts for the present invention may be formed by replacing a hydrogen ion of a moiety with a cation, such as $K^+$, $Na^+$, $Ca^{2+}$, $Mg^{2+}$, etc. In addition, other suitable methods of generating salts are specified throughout this specification and are within the scope of the present definition. For the purposes of the present invention, the specific identity of the cation used for forming the salt is of lesser importance than the chemical structure of the anion of which the salt is formed.

As used herein, "food article" refers to perishable or nonperishable foods such as meats, fruits and vegetables, and also refers to other foods such as grains and dairy products. In preferable embodiments, the food articles referred to herein are those which are perishable or prone to spoilage upon exposure to microbes or other pathogens. In addition, a "consumable product" is meant to refer to food articles, fluids for drinking, medicines for ingestion, or any other product introduced internally via any means into a human or animal.

As used herein, the term "antimicrobial" is used in its general sense to refer to the property of the described compound, product, composition, or article to prevent or reduce the growth, spread, formation, or other livelihood of organisms such as bacteria, viruses, protozoa, molds, or other organisms likely to cause spoilage or infection.

As used herein, the term "medical article" is used to refer to any suitable substrate which is or may come into contact with medical patients (human or animal), medical caregivers, bodily fluids, or any other source of contamination or infection generally associated with hospitals, clinics, physician's offices, etc.

As used herein, the term "stabilizer" is used to refer to carbonates. Such compounds have been found to stabilize the organosilanes of the invention by preventing self-condensation or other inactivation of the resulting compounds and products and simplifying transportation, dilution with water, and stabilization in water.

With these definitions in mind, the present invention provides the product formed from mixing an organosilane of the formula $R_nSiX_{4-n}$ where n is an integer of from 0 to 3, preferably 0 to 2; each R is, independently, a nonhydrolizable organic group; and each X is, independently, a hydrolyzable group; with an organic carbonate.

More preferably, in the above product, n is an integer from 0 to 2, preferably 1; each R is, independently, alkyl, preferably of from 1 to 22 carbon atoms branched or unbranched, substituted or unsubstituted, more preferably of from 1 to 6 carbon atoms or from 10 to 20 carbon atoms, most preferably of from 1 to 4 carbon atoms or of from 14 to 18 carbon atoms; alkyl alcohol of similar carbon lengths, branching, and substitution, or aromatic, such as benzyl, phenyl, etc.; each X is, independently, hydroxy, alkoxy, halogen (such as, but not limited to, Cl, Br, I, or F), acetyl, acetoxy, acyl, acyloxy, a hydroxylated solid or liquid polymeric moiety, polyglycol or polyalkylether; and carbonate stabilizers according to the invention are described by formula Ia and Ib:

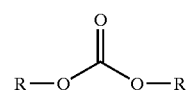

(Ia)

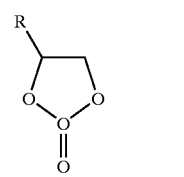

(Ib)

where each R is, independently,
  alkyl; of from 1 to 24 carbon atoms,
  ethylene glycol, propylene glycol, butyl glycol, pentyl glycol, hexyl glycol, alkyl glycol with 2 to 24 carbon atoms,
  aromatic, heteroaromatic, saturated and unsaturated aliphatic cyclic molecule, each with ring sizes of from 3 to 8 carbon atoms and in addition in hetero-cycles N, O, S in place of carbon atoms in any number and combination,
  alkyl alcohol, polyethylene glycol, polypropylene glycol, block and co-polymers of ethylene and propylene glycol and block and copolymers of ethylene glycol, propylene glycol, butyl glycol, pentyl glycol, hexyl glycol, alkyl glycol with 2 to 24 carbon atoms,
  alkyl triol with 3 to 24 carbon atoms, alkyl tetrol with 4 to 24 carbon atoms, and alkyl pentol with 5 to 24 carbon atoms and alkyl hexol with 6 to 24 carbon atoms,
  aromatic alcohol, heteroaromatic alcohol, saturated and unsaturated aliphatic cyclic alcohol, each with ring sizes of from 3 to 8 carbon atoms and in addition in hetero-cycles N, O, S in place of carbon atoms in any number and combination, with from 1 to 6 hydroxyl groups on the cyclic alcohol, and substitution on the ring by $(R_3)_x$ with x being an integer from 0 to 3, where $R_3$ is independently, a $(OH)_y$ substituted alkyl from 1 to 24 carbon atoms where y is an integer from 0 to 6.

The molecular weight of the carbonate is up to approximately 10,000 grams/mol average molecular weight.

In a further embodiment of the invention, the invention provides the product described above, wherein the organosilane is of the formula II, III, IV or V

  (II)

  (III)

  (IV)

  (V)

wherein each $R_1$ is independently, halogen or $R_6O$, where $R_6$ is H, alkyl of from 1 to about 24 carbon atoms, acetyl, acetoxy, acyl, acyloxy, propylene glycol, ethylene glycol, polyethylene glycol, polypropylene glycol, block and copolymers of ethylene and propylene glycol, the alkyl monoether of from 1 to 24 carbons of the following: propylene glycol, ethylene glycol, polyethylene glycol, polypropylene glycol, block and copolymers of ethylene and propylene glycol; or the monoester of a carbonic acid of from 1 to 24 carbons and at least one of the following: propylene glycol, ethylene glycol, polyethylene glycol, polypropylene glycol, block and copolymers of ethylene and propylene glycol; sorbitan esters and their ethers;

phenolic compounds substituted with an alkyl of from about 1 to 24 carbons, such as octyphenol, and nonylphenol, and their ethers;

$R_{35}$ is $R_6$, H, halogen (such as Cl, Br, F, or I), $NH_2(CH_2)_2NHR_2$, $NH_2R_2$, $C_3H_5O_2R_2$, $C_4H_5O_2R_2$, $NaO(CH_3O)P(O)R_2$, or $ClCH_2C_6H_4R_2$;

$R_{36}$ and $R_{37}$ are, independently, $R_{35}$, halogen, H, alkyl, preferably of from 1 to 4 carbon atoms, more preferably of from 1 to 2 carbon atoms, isobutyl, phenyl, or n-octyl;

$R_2$ is $R_6$, benzyl, vinyl or alkyl;

$R_3$ and $R_4$ are, independently, $R_{35}$, alkyl alcohol, alkoxy, alkyl of from 1 to 24 carbon atoms, preferably 1 to about 10 carbon atoms, more preferably alkyl of from 1 to 4 carbon atoms, or more preferably of from 1 to 2 carbon atoms;

$R_3$ and $R_4$ can, together, form a morpholine or cyclic or heterocyclic, unsaturated or saturated, five to seven-membered ring of the formula VI:

  (VI)

where k in an integer from 0 to 2, preferably 0 to 1, most preferably 1, $R_7$, where the ring is saturated is $CH_3$, O, S, NH, $NH_2^+$, $NCH_2CH_2NH_2$, $NCH_2CH_2NH_5^+$, $NCH_2CH_2N(R_8)(R_9)$, $NCH_2CH_2N^+(R_8)(R_9)(R_{10})$, N(alkyl), N(aryl), N(benzyl), where each $R_8$, $R_9$, and $R_{10}$ is independently, benzyl, $R_{37}$, polyglycol, preferably of from 1 to 4 carbon atoms, alkyl alcohol, preferably of from 1 to 4 carbon atoms, alkoxy, preferably of from 1 to 4 carbon atoms, or alkyl, from 1 to 24 carbon atoms, preferably 1 to about 10 carbon atoms, and the "alkyl" specified above is of from 1 to 3 carbon atoms, the "aryl" is more preferably phenyl or benzyl, and $R_7$, where the ring is unsaturated is CH, N, $N^+H$, $N^+$(alkyl), $N^+$(aryl), $N^+$(benzyl), $N—CH_2—N$, $N^+H—CH_2—N$, $N^+$(alkyl)-$CH_2$—N, or $N^+$(benzyl)-$CH_2$—N, where the alkyl, aryl, or benzyl is as described above; wherein the ring is unsubstituted or substituted with alkyl of from 1 to 24 carbon atoms, more preferably of from 1 to 10 carbon atoms, most preferably of from 1 to 3 carbon atoms, ester, aldehyde, carboxylate (preferably acetoxy, acetyl, acyl, acyloxy or perfluorocarboxylate) amide, thionamide, nitro, amine, or halide, most preferably Cl, Br, or I. Alternatively, the ring provided by formula VI represents $R_3$ or $R_4$, independently. The nitrogen in formula II or III that is part of the ring structure of formula VI is replaced by CH or $CH_2$ or saturated with hydrogen or alkyl substitution of from 1 to about 24 carbons by removal of a positive charge. This ring is attached to the nitrogen in structure II or III, by removing any one hydrogen from the structure and placing a bond from the nitrogen of II or III to the atom missing the hydrogen.

$R_5$ is alkyl alcohol, preferably of from 1 to 6 carbon atoms, more preferably of from 1 to 4 carbon atoms, $R_{35}$, $CH_2C_6H_5$, polyglycol, such as a polyethylene glycol or a polypropylene glycol, alkyl of from 1 to 24 carbon atoms, preferably of from 1 to 10 carbon atoms, most preferably of from 1 to 6 carbon atoms, alkoxy, of from 1 to 24 carbon atoms, more preferably of from 1 to 10 carbon atoms, most preferably of from 1 to 6 carbon atoms, perfluoroalkyl, of from 1 to 24 carbon atoms, more preferably of from 1 to 10 carbon atoms, most preferably of from 1 to 6 carbon atoms, perfluoroalkylsulfonate, of from 1 to 24 carbon atoms, more preferably of from 1 to 10 carbon atoms, most preferably of from 1 to 6 carbon atoms, perfluoroalkylcarboxylate, or is a five to seven-membered ring of formula VI as described above; and $Y^-$ is a suitable anionic moiety to form salts of the compound of formula II, III, IV, and V.

This invention provides a water stable composition, comprising water and an organosilane of interest, mixed with carbonate.

The present invention provides a composition for treating a substrate, comprising a carrier and an effective amount of an organosilane of interest and a carbonate as described herein. The carrier may be water, or in further embodiments, the carrier is other than water.

Moreover, the present invention also provides a product resulting from mixing an organosilane of the formula II, III, IV, or V:

  (II)

  (III)

  (IV)

  (V)

as substantially previously described with reference to the formula numbers II, III, IV and V, with carbonate stabilizers according to the invention as described above.

In addition, the present invention also provides a method of treating a substrate, comprising contacting the substrate with a sufficient amount of the composition as described above for a period of time sufficient for treatment of the substrate. Moreover, in an alternate embodiment, the present invention provides a method of treating a substrate, comprising contacting the substrate with a sufficient amount of the compound as described above for a period of time sufficient for treatment of the substrate.

In addition, the present invention provides a treated substrate having adhered thereto the product produced by contacting the organosilane and the carbonate as described above. Alternatively, the present invention provides a treated substrate having adhered thereto a compound produced by contacting the organosilane and the carbonate as described above.

In yet another embodiment, the present invention provides a method of dyeing and treating a substrate, comprising contacting the substrate with an aqueous (i.e., substantially water soluble) composition comprising an aqueous soluble dye suitable for dyeing a substrate and the product formed from mixing an organosilane of interest with an organic carbonate.

In yet another embodiment, the present invention provides a method of antimicrobially treating a substrate selected from the group consisting of a concrete pipe, food article, fluid container, glove, shower curtain, shower door, latex medical article, a tooth brush, a comb, a hair brush, a denture, an orthodontic retainer, a spa or pool filter, an air filter, an HVAC air system, a cabin air system, a marble article, a statue, an exposed work of art, a PP, PE or polyester plastic cover, a silicone or TEFLON® coated fiberglass article, a Dryvitt finish, a stucco finish, blended cotton, a bio-film, a bio-adhesive, a single ply roofing, a roofing shingle, and a fiberglass reinforcement product, comprising contacting the substrate with an effective amount of the product formed from mixing an antimicrobial organosilane of interest with an organic carbonate.

A further embodiment of the present invention provides a method of antimicrobially enhancing a product of rubbing alcohol, a flower preservative, or a waterproofing solution, comprising admixing with the product an effective amount of the product formed from mixing an antimicrobial organosilane of interest with an organic carbonate.

The present invention provides water-stabilized and solubilized organosilane compounds, products, and compositions, methods of their use, and articles prepared using the compounds, products, and compositions. In particular, the present invention is useful in stabilizing a broad variety of organosilanes of the general formula $R_nSiX_{4-n}$ where n is an integer of from 0 to 3, preferably 0 to 2; R is a nonhydrolizable organic group, such as but not limited to, alkyl, aromatic, organofunctional, or a combination thereof, and X is halogen, such as but not limited to, Cl, Br, or I, or X is hydroxy, alkoxy such as methoxy or ethoxy, acetoxy, or unsubstituted or substituted acyl or acyloxy. For such organosilanes, X is prone to react with various hydroxyl containing molecules.

In a further embodiment, the present invention employs a carbonate as solvent. The silane and carbonate mixture are stable. The carbonate silane mixtures often are less flammable than methanol mixtures and are easier to dissolve in water than many silanes in methanol.

Alternatively, where the stabilizers are not sufficiently water-soluble, additional stability is achieved by mixing the organosilane with the stabilizer in a non-aqueous solvent. In such an alternative preparation, the remaining solvent (e.g., methanol) is liberated via distillation, freeze-drying, evaporation or other methods known in the art for removal of volatile organic solvents. For carbonates within this invention that are themselves not very soluble in water, an organosilane-stabilizing effect in water may still be achieved by admixing the organosilane with, for example, a carbonate in water, followed by filtration.

The solutions are stable for extended periods, from several days to several months. It will also be recognized that while aqueous silane stock solutions of up to 45% silane may be stabilized by carbonates disclosed herein, working silane concentrations tend to be in the 0.001–10% silane range where the stabilization effects of the herein disclosed stabilizers are less challenged by the higher silane concentrations required in stock solutions. Acid pHs appear to be preferred, but not required, for stability of the solutions of the subject invention.

The solutions of the present invention are, in certain preferred embodiments, useful for the application of various organosilane coupling agents to surfaces in industrial and household uses without the use of toxic and/or flammable organic solvents. One of ordinary skill in the art would recognize that the above preparation steps are merely guidelines and such a person would, without undue experimentation, be able to prepare the composition by varying the parameters for contacting or mixing the organosilane and the polyol and order of introduction of reagents and starting materials without deviating from the basic and novel characteristics of the present invention.

Silanes

The present invention is useful for stabilizing organosilanes of the general formula $R_nSiN_{4-n}$ where n is an integer of from 0 to 3, preferably 0 to 2; R is a nonhydrolizable organic group (alkyl aromatic, organofunctional or a combination thereof); and X is hydroxy, alkoxy, preferably methoxy or ethoxy, halogen, preferably Cl, Br, or I, acetoxy, acyl or substituted acyl, acyloxy, or a hydrolyzable polymer or other moiety prone to hydrolysis and/or environmental harmfulness.

The organosilanes used in the practice of the present invention need not be, and often are not, water soluble. By varying the stabilizer and preparation method, the organosilanes selected for use in the present invention are solubilized in water by the stabilizer.

Numerous art-known organosilanes are suitable for the present stabilization procedures to produce water-stabilized compounds, products and compositions. U.S. Pat. Nos. 5,411,585; 5,064,613; 5,145,592, and the publication entitled "A Guide to DC Silane Coupling Agent" (Dow Corning, 1990) disclose many suitable organosilanes. The contents of these references are hereby incorporated in their entirety herein by this reference for the teachings of suitable organosilanes. These organosilanes are suitable for the formation of the water-stabilized organosilane compounds, products and compositions of the present invention. In addition, the disclosure of U.S. Pat. No. 4,390,712 is hereby incorporated by reference for its teaching of siloxane synthesis in an aqueous medium. Per the instant disclosure, those skilled in the art will appreciate that the aqueous siloxane synthesis methods of the U.S. Pat. No. 4,390,712 patent are modified to advantage by performing the siloxane synthesis in the presence of the carbonate stabilizer as defined herein, thereby forming a stabilized siloxane-water composition while still taking advantage of the accelerated kinetics of siloxane formation in aqueous media noted in the U.S. Pat. No. 4,390,712 patent. Accordingly, a further embodiment of this invention is a method for making an organosilane of the formula $R_nSiX_{4-n}$ where n is an integer of from 0 to 3, preferably 0 to 2; each R is, independently, a nonhydrolizable organic group; and each X is, independently, a hydrolyzable group; from starting materials in an aqueous solution in the presence of an effective amount of carbonate sufficient to stabilize the organosilane as it is formed from the reactants. In the instant application we disclose the finding that compounds having at least one carbonate group stabilize aqueous organosilane solutions. The archetypal example of carbonate of the instant invention is propylene carbonate with an organic carbonate.

Preferred silanes for use in the compounds, products and compositions and methods of the present invention include silanes of the following formula:

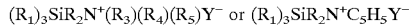

$(R_1)_3SiR_2N^+(R_3)(R_4)(R_5)Y^-$ or $(R_1)_3SiR_2N^+C_5H_5Y^-$ wherein each $R_1$ is, independently, halogen [Cl, Br, I, F] or $R_6O$, where $R_6$ is H, alkyl of from 1 to about 6 carbon atoms, unsubstituted or substituted, preferably from 1 to about 2 carbon atoms and more preferably 1 carbon atom, or acetyl- or other acyl, including substituted acyl and acyloxy; or $R_6O$ can be derived from any hydroxylated polymer, hydroxylated liquid, or hydroxylated solid regardless of water solubility; or $R_6O$ can be derived from any polyglycol such as, but not limited to, polyethyleneglycols or polypropyleneglycols, such as poly(propyleneglycol)triol (glycerol propoxylate); $R_2$ is unsubstituted or substituted benzyl- or an unsubstituted or substituted alkyl of from 1 to about 3 carbon atoms, preferably alkyl of from 1 to 3 carbon atoms; $R_3$ and $R_4$ are, independently, lower alkoxy of from 1 to 4 carbon atoms, preferably of 2 carbon atoms, such as $CH_2CH_2OH$, $CH_2CH(OH)CH_3$, alkyl of from 1 to about 22 carbon atoms, preferably from 1 to about 10 carbon atoms and most preferably from 1 to 2 carbon atoms or $R_3$ and $R_4$ can, together, form a morpholine or other cyclic or heterocyclic, unsaturated or saturated, five to seven-membered ring of the formula:

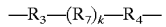

$—R_3—(R_7)_k—R_4—$ where k is an integer from 0 to 2 and $R_7$, where the ring is saturated, is $CH_2$, O, S, NH, $NH_2^+$, $NCH_2CH_2NH_2$, $NCH_2CH_2NH_3^+$, $NCH_2CH_2N(R_8)(R_9)$, $NCH_2CH_2N^+(R_8)(R_9)(R_{10})$, N(alkyl), N(aryl), N(benzyl), and $R_7$, where the ring is unsaturated is, N, $N^+H$, $N^+$(alkyl), $N^+$(aryl), $N^+$(benzyl), $N—CH_2—N$, $N^+H—CH_2—N$, $N^+$(alkyl)-$CH_2—N$, $N^+$(aryl)-$CH_2—N$, or $N^+$(benzyl)-$CH_2—N$ where $R_8$, $R_9$, and $R_{10}$ are, independently, benzyl, polyglycol, lower alkyl alcohol of from 1 to 4 carbon atoms, lower alkoxy of from 1 to 4 carbon atoms, or alkyl of from 1 to about 22 carbon atoms, preferably 1 to about 10 carbon atoms; $R_5$ is $CH_2C_6H_5$, $CH_2CH_2OH$, $CH_2CH(OH)CH_3$, a polyglycol such as polyethyleneglycol: $—(CHCH_2O)H$, polypropyleneglycol: $—(CH_2CH(CH_3)O)_aH$, or alkylated polyoxyethylene: $—(CH_2CH_2O)_aB$ where B is alkyl of from 1 to 22 carbon atoms, unsubstituted or substituted, and where each a is, independently, an integer of from 1 to 12, more preferably of from about 1 to about 5, or $R_5$ is alkyl or perfluoroalkyl of from 1 to about 22 carbon atoms, preferably from about 12 to about 20 carbon atoms and even more preferably from 14 to about 18 carbon atoms; and Y is halogen (such as Cl, Br, I), acetate, sulfate, tosylate or carboxylate, such as acetate, polycarboxylate salts, alcoholates, functionalized carboxylate, such as trifluoroacetate and perfluoroalkylcarboxylates, or other alkyl and arylsulfonate salts, including trifluoromethylsulfonate and anionic metal oxides, perfluoroalkylsulfonate salts, phosphate and phosphonate salts, borate and boronate salts, benzoates or any other suitable anionic moiety and the ring provided for formula V represents $R_3$ or $R_4$, independently, with the ring nitrogen of formula II or III replaced by CH or $CH_2$. This ring is attached to the nitrogen in structure II or III, by removing any one hydrogen from the structure and placing a bond from the nitrogen of II or III to the atom missing the hydrogen.

Preferred organosilanes include, but are not limited to:

3-(trimethoxysilyl)propyldimethyloctadecyl ammonium chloride, 3-(trimethoxysilyl)propylmethyldi(decyl) ammonium chloride, 3-chloropropyltrimethylsilane, octadecyltrimethoxysilane, perfluorooctyltriethoxysilane, $(CH_3O)_3Si(CH_2)_3N^+(CH_3)_2C_{18}H_{37}Cl^-$, $(CH_3O)_3Si(CH_2)_3N^+(CH_3)_2C_{18}H_{37}Br^-$, $(CH_3O)_3Si(CH_2)_3N^+(C_{10}H_{21})CH_3Cl^-$, $(CH_3O)_3Si(CH_2)_3N^+(C_{10}H_{21})CH_3Br^-$, $(CH_3O)_3Si(CH_2)_3N^+(CH_3)_3Cl^-$, $(CH_3O)_3Si(CH_2)_3N^+(CH_3)_2C_8H_{17}Cl^-$, $(CH_3O)_3Si(CH_2)_3N^+(CH_3)_2C_{10}H_{21}Cl^-$, $(CH_3O)_3Si(CH_2)_3N^+(CH_3)_2C_{12}H_{25}Cl^-$, $(CH_3O)_3Si(CH_2)_3N^+(CH_3)_2C_{14}H_{29}Cl^-$, $(CH_3O)_3Si(CH_2)_3N^+(CH_3)_2C_{16}H_{33}Cl^-$, $(CH_3O)_3Si(CH_2)_3N^+(CH_3)_2C_{20}H_{41}Cl^-$, $(CH_3O)_3Si(CH_2)_3N^+(CH_4H_9)_3Cl^-$, $(CH_3O)_3Si(CH_2)_3N^+(C_2H_5)_3Cl^-$, $(CH_3CH_2O)_3Si(CH_2)_3N^+(CH_3)_2C_{18}H_{27}Cl^-$, $(CH_3O)_3Si(CH_2)_3NHC(O)(CF_2)_6CF_3$, $(CH_3O)_3Si(CH_2)_3NHC(O)(CF_2)_8CF_3$, $(CH_3O)_3Si(CH_2)_3NHC(O)(CF_2)_8CF_3$, $(CH_3O)_3Si(CH_2)_3NHC(O)(CF_2)_{12}CF_3$, $(CH_3O)_3Si(CH_2)_3NHC(O)(CF_2)_{14}CF_3$, $(CH_3O)_3Si(CH_2)_3NHC(O)(CF_2)_{16}CF_3$, $(CH_3O)_3Si(CH_2)_3NHSO_2(CF_2)_7CF_3$, $(CH_3O)_3Si(CH_2)_3N^+(CH_3)_2(CH_2)_3NHC(O)(CH_2)_6CH_3$, $(CH_3O)_3Si(CH_2)_3N^+(CH_3)_2(CH_2)_3NHC(O)(CH_2)_8CH_3$, $(CH_3O)_3Si(CH_2)_3N^+(CH_3)_2(CH_2)_3NHC(O)(CH_2)_{10}CH_3$, $(CH_3O)_3Si(CH_2)_3N^+(CH_3)_2(CH_2)_3NHC(O)(CH_2)_{12}CH_3$, $(CH_3O)_3Si(CH_2)_3N^+(CH_3)_2(CH_2)_3NHC(O)(CH_2)_{14}CH_3$, $(CH_3O)_3Si(CH_2)_3N^+(CH_3)_2(CH_2)_3NHC(O)(CH_2)_{16}CH_3$, $(CH_3O)_3Si(CH_2)_3N^+(CH_3)_2(CH_2)_3NHC(O)(CF_2)_6CF_3$, $(CH_3O)_3Si(CH_2)_3N^+(CH_3)_2(CH_2)_3NHC(O)(CF_2)_8CF_3$, $(CH_3O)_3Si(CH_2)_3N^+(CH_3)_2(CH_2)_3NHC(O)(CF_2)_{10}CF_3$, $(CH_3O)_3Si(CH_2)_3N^+(CH_3)_2(CH_2)_3NHC(O)(CF_2)_{12}CF_3$, $(CH_3O)_3Si(CH_2)_3N^+(CH_3)_2(CH_2)_3NHC(O)(CF_2)_{14}CF_3$, $(CH_3O)_3Si(CH_2)_3N^+(CH_3)_2(CH_2)_3NHC(O)(CF_2)_{16}CF_3$, $(CH_3O)_3Si(CH_2)_3N^+(CH_3)_2(CH_2)_3NHC(O)(CF_2)_7CF_3$, $(CH_3O)_3Si(CH_2)_3N^+(CH_3)_2(CH_2)_3NHSO_2(CF_2)_9CF_3$, $(CH_3O)_3Si(CH_2)_3N^+(CH_3)_2(CH_2)_3NHSO_2(CF_2)_{11}CF_3$, $(CH_3O)_3Si(CH_2)_3N^+(CH_3)_2(CH_2)_3NHSO_2(CF_2)_{13}CF_3$, $(CH_3O)_3Si(CH_2)_3N^+(CH_3)_2(CH_2)_3NHSO_2(CF_2)_{15}CF_3$, $(CH_3O)_3Si(CH_2)_3N^+(CH_3)_2(CH_2)_3NHSO_2(CF_2)_{16}CF_3$, aminoethylaminopropyltrimethoxysilane: $NH_2(CH_2)_2NH(CH_2)_3Si(OCH_3)_3$, 3-aminopropyltrimethoxysilane: $NH_2(CH_2)_3Si(OCH_3)_3$, 3-aminopropyltriethoxysilane: $NH_2(CH_2)_3Si(OCH_2CH_3)_3$, 3-chloropropyltrimethoxysilane: $Cl(CH_2)_3Si(OCH_3)_3$, 3-chloropropyltriethoxysilane: $Cl(CH_2)_3Si(OCH_2CH_3)_3$, 3-chloropropyltrichlorosilane: $Cl(CH_2)_3SiCl_3$, 3-glycidoxypropyltrimethoxysilane: $C_3H_5O_2(CH_2)_3Si(OCH_3)_3$,
3-glycidoxypropyltriethoxysilane: $C_3H_5O_2(CH_2)_3Si(OCH_2CH_3)_3$,
3-methacryloxypropyltriethoxysilane: $C_4H_5O_2(CH_2)_3Si(OCH_2CH_3)_3$,
3-methacryloxypropyltrimethoxysilane: $C_4H_5O_2(CH_2)_3Si(OCH_2CH_3)_3$,
methyldichlorosilane: $CH_3SiHCl_2$,
silane-modified melamine: Dow Corning Q1-6106,
sodium (trihydroxysilyl)propylmethylphosphonate: $NaO(CH_3O)P(O)(CH_2)_3Si(OH)_3$,
trichlorosilane, $SiHCl_3$,
n-2-vinylbenzylamino-ethyl-3-aminopropyltrimethoxysilane HCL: Dow Corning Z-6032,
vinyltriacetoxysilane: $H_2C=CHSi(OCOCH_3)_3$,
vinyltrimethoxysilane: $H_2C=CHSi(OCH_3)_3$,
vinyltriethoxysilane: $H_2C=CHSi(OCH_2CH_3)_3$,
vinyltrichlorosilane: $H_2C=CHSiCl_3$,
dimethyldichlorosilane: $(CH_3)_2SiCl_2$,
dimethyldimethoxysilane: $(CH_3)_2Si(OCH_3)_2$,
diphenyldichlorosilane: $(C_6H_5)_2SiCl_2$,
ethyltrichlorosilane: $(C_2H_5)SiCl_3$,
ethyltrimethoxysilane: $(C_2H_5)Si(OCH_3)_3$,
ethyltriethoxysilane: $(C_2H_5)Si(OCH_2CH_3)_3$,
isobutyltrimethoxysilane,
n-octyltriethoxysilane,
methylphenyldichlorosilane: $CH_3(C_6H_5)SiCl_2$,
methyltrichlorosilane: $CH_3SiCl_3$,
methyltrimethoxysilane: $CH_3Si(OCH_3)_3$,
phenyltrichlorosilane: $C_6H_5SiCl_3$,
phenyltrimethoxysilane: $C_6H_5Si(OCH_3)_3$,
n-propyltrichlorosilane: $C_3H_7SiCl_3$,
n-propyltrimethoxysilane: $C_3H_7Si(OCH_3)_3$,
silicon tetrachloride: $SiCl_4$,
$ClCH_2C_6H_4CH_2CH_2SiCl_3$,,
$ClCH_2C_6H_4CH_2CH_2Si(OCH_3)_3$,
$ClCH_2C_6H_4CH_2CH_2Si(OCH_2CH_3)_3$,
decyltrichlorosilane,
dichloromethyl(4-methylphenethyl)silane,
diethoxymethylphenylsilane,
[3-(diethylamino)propyl]trimethoxysilane,
3-(dimethoxymethylsilyl)-1-propanethiol,
dimethoxymethylvinylsilane,
3-[tris(trimethylsilyloxy)silyl]propyl methacrylate,
trichloro[4-(chloromethyl)phenyl]silane,
methylbis(trimethylsilyloxy)vinylsilane,
methyltripropoxysilane, and
trichlorocyclopentylsilane.

In one particular embodiment of this invention, namely the use of the organosilane as a UV protectant, for example, in a sun-tan lotion, para-amino benzoic acid, cinnamic acid, benzoic acid and benzophenone are active ingredients. These compounds and their alkyl derivatives attached to a siloxane are part of this invention. Some examples are:

$(CH_3O)_3Si(CH_2)_3NHC_6H_4COOH$
$(CH_3O)_3Si(CH_2)_3NHC_6H_4COOCH_3$
$(CH_3O)_3Si(CH_2)_3NHC_6H_4COOC_2H_5$
$(CH_3O)_3Si(CH_2)_3NHC_6H_4COOC_3H_7$
$(CH_3O)_3Si(CH_2)_3NHC_6H_4COOC_4H_9$
$(CH_3O)_3Si(CH_2)_3NHC_6H_4COOCH_2C_6H_5$
$(CH_3O)_3Si(CH_2)_3NHC_6H_4COOCH_2C_6H_4NH_2$
$(CH_3O)_3Si(CH_2)_3NHC_6H_4COOCH_2C_6H_4N(CH_3)_2$
$(CH_3O)_3Si(CH_2)_3NHC_6H_4COOCH_2C_6H_4N(CH_2CH_3)_2$
$(CH_3O)_3Si(CH_2)_3NHC_6H_4COOCH_2C_6H_4N^+(CH_3)_3\ Y^-$
$(CH_3O)_3Si(CH_2)_3NHC_6H_4COOCH_2C_6H_4N^+(C_2CH_3)_3\ Y^-$
$(CH_3O)_3Si(CH_2)_3NCH_3C_6H_4COOH$
$(CH_3O)_3Si(CH_2)_3NCH_3C_6H_4COOCH_3$
$(CH_3O)_3Si(CH_2)_3NCH_3C_6H_4COOC_2H_5$
$(CH_3O)_3Si(CH_2)_3NCH_3C_6H_4COOC_3H_7$
$(CH_3O)_3Si(CH_2)_3NCH_3C_6H_4COOC_4H_9$
$(CH_3O)_3Si(CH_2)_3NCH_3C_6H_4COOCH_2C_6H_5$
$(CH_3O)_3Si(CH_2)_3NCH_3C_6H_4COOCH_2C_6H_4NH_2$
$(CH_3O)_3Si(CH_2)_3NCH_3C_6H_4COOCH_2C_6H_4N(CH_3)_2$
$(CH_3O)_3Si(CH_2)_3NCH_3C_6H_4COOCH_2C_6H_4N(CH_2CH_3)_2$
$(CH_3O)_3Si(CH_2)_3NCH_3C_6H_4COOCH_2C_6H_4N^+(CH_3)_3\ Y^-$
$(CH_3O)_3Si(CH_2)_3NCH_3C_6H_4COOCH_2C_6H_4N^+(CH_2CH_3)_3\ Y^-$
$(CH_3O)_3Si(CH_2)_3N^+(CH_3)_2C_6H_4COOH\ Y^-$
$(CH_3O)_3Si(CH_2)_3N^+(CH_3)_2C_6H_4COOCH_3\ Y^-$
$(CH_3O)_3Si(CH_2)_3N^+(CH_3)_2C_6H_4COOC_2H_5\ Y^-$
$(CH_3O)_3Si(CH_2)_3N^+(CH_3)_2C_6H_4COOC_3H_7\ Y^-$
$(CH_3O)_3Si(CH_2)_3N^+(CH_3)_2C_6H_4COOC_4H_9\ Y^-$
$(CH_3O)_3Si(CH_2)_3N^+(CH_3)_2C_6H_4COOCH_2C_6H_5\ Y^-$
$(CH_3O)_3Si(CH_2)_3N^+(CH_3)_2C_6H_4COOCH_2C_6H_4NH_2\ Y^-$
$(CH_3O)_3Si(CH_2)_3N^+(CH_3)_2C_6H_4COOCH_2C_6H_4N(CH_3)_2\ Y^-$
$(CH_3O)_3Si(CH_2)_3N^+(CH_3)_2C_6H_4COOCH_2C_6H_4N(CH_2CH_3)_2\ Y^-$
$(CH_3O)_3Si(CH_2)_3N^+(CH_3)_2C_6H_4COOCH_2C_6H_4N^+(CH_3)_3\ Y^-Y^-$
$(CH_3O)_3Si(CH_2)_3N^+(CH_3)_2C_6H_4COOCH_2C_6H_4N^+(CH_2CH_3)_3\ Y^-Y^-$
$(CH_3O)_3Si(CH_2)_3NC_2H_5C_6H_4COOH$
$(CH_3O)_3Si(CH_2)_3NC_2H_5C_6H_4COOCH_3$
$(CH_3O)_3Si(CH_2)_3NC_2H_5C_6H_4COOC_4H_9$
$(CH_3O)_3Si(CH_2)_3NC_2H_5C_6H_4COOC_3H_7$
$(CH_3O)_3Si(CH_2)_3NC_2H_5C_6H_4COOC_4H_9$
$(CH_3O)_3Si(CH_2)_3NC_2H_5C_6H_4COOCH_2C_6H_5$
$(CH_3O)_3Si(CH_2)_3NC_2H_5C_6H_4COOCH_2C_6H_4NH_2$
$(CH_3O)_3Si(CH_2)_3NC_2H_5C_6H_4COOCH_2C_6H_4N(CH_3)_2$
$(CH_3O)_3Si(CH_2)_3NC_2H_5C_6H_4COOCH_2C_6H_4N(CH_2CH_3)_2$
$(CH_3O)_3Si(CH_2)_3NC_2H_5C_6H_4COOCH_2C_6H_4N^+(CH_3)_3\ Y^-$
$(CH_3O)_3Si(CH_2)_3NC_2H_5C_6H_4COOCH_2C_6H_4N^+(CH_2CH_3)_3\ Y^-$
$(CH_3O)_3Si(CH_2)_3N^+(C_2H_5)_2C_6H_4COOH\ Y^-$
$(CH_3O)_3Si(CH_2)_3N^+(C_2H_5)_2C_6H_4COOCH_3\ Y^-$
$(CH_3O)_3Si(CH_2)_3N^+(C_2H_5)_2C_6H_4COOC_2H_5\ Y^-$
$(CH_3O)_3Si(CH_2)_3N^+(C_2H_5)_2C_6H_4COOC_3H_7\ Y^-$
$(CH_3O)_3Si(CH_2)_3N^+(C_2H_5)_2C_6H_4COOC_4H_9\ Y^-$
$(CH_3O)_3Si(CH_2)_3N^+(C_2H_5)_2C_6H_4COOCH_2C_6H_5\ Y^-$ (CH₃O)₃Si(CH₂)₃N⁺(C₂H₅)₂C₆H₄COOCH₂C₆H₄N₂ Y⁻
(CH₃O)₃Si(CH₂)₃N⁺(C₂H₅)₂C₆H₄COOCH₂C₆H₄N(CH₃)₂ Y⁻
(CH₃O)₃Si(CH₂)₃N⁺(C₂H₅)₂C₆H₄COOCH₂C₆H₄N(CH₂CH₃)₂ Y⁻
(CH₃O)₃Si(CH₂)₃N⁺(C₂H₅)₂C₆H₄COOCH₂C₆H₄N⁺(CH₃)₃ Y⁻Y⁻
(CH₃O)₃Si(CH₂)₃N⁺(C₂H₅)₂C₆H₄COOCH₂C₆H₄N⁺(CH₂CH₃)₃ Y⁻Y⁻
(CH₃CH₂O)₃Si(CH₂)₃NHC₆H₄COOH
(CH₃CH₂O)₃Si(CH₂)₃NHC₆H₄COOCH₃
(CH₃CH₂O)₃Si(CH₂)₃NHC₆H₄COOC₂H₅
(CH₃CH₂O)₃Si(CH²)₃NHC₆H₄COOC₃H₇
(CH₃CH₂O)₃Si(CH₂)₃NHC₆H₄COOC₄H₉
(CH₃CH₂O)₃Si(CH₂)₃NHC₆H₄COOCH₂C₆H₅
(CH₃CH₂O)₃Si(CH₂)₃NHC₆H₄COOCH₂C₆H₄NH₂
(CH₃CH₂O)₃Si(CH₂)₃NHC₆H₄COOCH₂C₆H₄N(CH₃)₂
(CH₃CH₂O)₃Si(CH₂)₃NHC₆H₄COOCH₂C₆H₄N(CH₂CH₃)₂
(CH₃CH₂O)₃Si(CH₂)₃NHC₆H₄COOCH₂C₆H₄N⁺(CH₃)₃ Y⁻
(CH₃CH₂O)₃Si(CH₂)₃NHC₆H₄COOCH₂C₆H₄N⁺(CH₂CH₃)₃ Y⁻
(CH₃CH₂O)₃Si(CH₂)₃NCH₃C₆H₄COOH
(CH₃CH₂O)₃Si(CH₂)₃NCH₃C₆H₄COOCH₃
(CH₃CH₂O)₃Si(CH₂)₃NCH₃C₆H₄COOC₂H₅
(CH₃CH₂O)₃Si(CH₂)₃NCH₃C₆H₄COOC₃H₇
(CH₃CH₂O)₃Si(CH₂)₃NCH₃C₆H₄COOC₄H₉
(CH₃CH₂O)₃Si(CH₂)₃NCH₃C₆H₄COOCH₂C₆H₅
(CH₃CH₂O)₃Si(CH₂)₃NCH₃C₆H₄COOCH₂C₆H₄NH₂
(CH₃CH₂O)₃Si(CH₂)₃NCH₃C₆H₄COOCH₂C₆H₄N(CH₃)₂
(CH₃CH₂O)₃Si(CH₂)₃NCH₃C₆H₄COOCH₂C₆H₄N(CH₂CH₃)₂
(CH₃CH₂O)₃Si(CH₂)₃NCH₃C₆H₄COOCH₂C₆H₄N⁺(CH₃)₃ Y⁻
(CH₃CH₂O)₃Si(CH₂)₃NCH₃C₆H₄COOCH₂C₆H₄N⁺(CH₂CH₃)₃ Y⁻
(CH₃CH₂O)₃Si(CH₂)₃N⁺(CH₃)₂C₆H₄COOH Y⁻
(CH₃CH₂O)₃Si(CH₂)₃N⁺(CH₃)₂C₆H₄COOCH₃ Y⁻
(CH₃CH₂O)₃Si(CH₂)₃N⁺(CH₃)₂C₆H₄COOC₂H₅ Y⁻
(CH₃CH₂O)₃Si(CH₂)₃N⁺(CH₃)₂C₆H₄COOC₃H₇ Y⁻
(CH₃CH₂O)₃Si(CH₂)₃N⁺(CH₃)₂C₆H₄COOC₄H₉ Y⁻
(CH₃CH₂O)₃Si(CH₂)₃N⁺(CH₃)₂C₆H₄COOCH₂C₆H₅ Y⁻
(CH₃CH₂O)₃Si(CH₂)₃N⁺(CH₃)₂C₆H₄COOCH₂C₆H₄NH₂ Y⁻
(CH₃CH₂O)₃Si(CH₂)₃N⁺(CH₃)₂C₆H₄COOCH₂C₆H₄N(CH₃)₂ Y⁻
(CH₃CH₂O)₃Si(CH₂)₃N⁺(CH₃)₂C₆H₄COOCH₂C₆H₄N(CH₂CH₃)₂ Y⁻
(CH₃CH₂O)₃Si(CH₂)₃N⁺(CH₃)₂C₆H₄COOCH₂C₆H₄N⁺(CH₃)₃ Y⁻Y⁻
(CH₃CH₂O)₃Si(CH₂)₃N⁺(CH₃)₂C₆H₄COOCH₂C₆H₄N⁺(CH₂CH₃ Y⁻Y⁻
(CH₃CH₂O)₃Si(CH₂)₃NC₂H₅C₆H₄COOH
(CH₃CH₂O)₃Si(CH₂)₃NC₂H₅C₆H₄COOCH₃
(CH₃CH₂O)₃Si(CH₂)₃NC₂H₅C₆H₄COOC₂H₅
(CH₃CH₂O)₃Si(CH₂)₃NC₂H₅C₆H₄COOC₃H₇
(CH₃CH₂O)₃Si(CH₂)₃NC₂H₅C₆H₄COOC₄H₉
(CH₃CH₂O)₃Si(CH₂)₃NC₂H₅C₆H₄COOCH₂C₆H₅
(CH₃CH₂O)₃Si(CH₂)₃NC₂H₅C₆H₄COOCH₂C₆H₄NH₂
(CH₃CH₂O)₃Si(CH₂)₃NC₂H₅C₆H₄COOCH₂C₆H₄N(CH₃)₂
(CH₃CH₂O)₃Si(CH₂)₃NC₂H₅C₆H₄COOCH₂C₆H₄N(CH₂CH₃)₂
(CH₃CH₂O)₃Si(CH₂)₃NC₂H₅C₆H₄COOCH₂C₆H₄N⁺(CH₃)₃ Y⁻
(CH₃CH₂O)₃Si(CH₂)₃NC₂H₅C₆H₄COOCH₂C₆H₄N⁺(CH₂CH₃)₃ Y⁻
(CH₃CH₂O)₃Si(CH₂)₃N⁺(C₂H₅)₂C₆H₄COOH Y⁻
(CH₃CH₂O)₃Si(CH₂)₃N⁺(C₂H₅)₂C₆H₄COOCH₃ Y⁻
(CH₃CH₂O)₃Si(CH₂)₃N⁺(C₂H₅)₂C₆H₄COOC₂H₅ Y⁻
(CH₃CH₂O)₃Si(CH₂)₃N⁺(C₂H₅)₂C₆H₄COOC₃H₇ Y⁻
(CH₃CH₂O)₃Si(CH₂)₃N⁺(C₂H₅)₂C₆H₄COOCH₂C₄H₉ Y⁻
(CH₃CH₂O)₃Si(CH₂)₃N⁺(C₂H₅)₂C₆H₄COOCH₂C₆H₅ Y⁻
(CH₃CH₂O)₃Si(CH₂)₃N⁺(C₂H₅)₂C₆H₄COOCH₂C₆H₄NH₂ Y⁻
(CH₃CH₂O)₃Si(CH₂)₃N⁺(C₂H₅)₂C₆H₄COOCH₂C₆H₄N(CH₃)₂ Y⁻
(CH₃CH₂O)₃Si(CH₂)₃N⁺(C₂H₅)₂C₆H₄COOCH₂C₆H₄N(CH₂CH₃)₂ Y⁻
(CH₃CH₂O)₃Si(CH₂)₃N⁺(C₂H₅)₂C₆H₄COOCH₂C₆H₄N⁺(CH₃)₃ Y⁻Y⁻, and
(CH₃CH₂O)₃Si(CH₂)₃N⁺(C₂H₅)₂C₆H₄COOCH₂C₆H₄N⁺(CH₂CH₃)₃ Y⁻Y⁻.

Stabilizers

Carbonate stabilizers according to the invention are described by formula Ia and Ib:

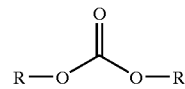
(Ia)

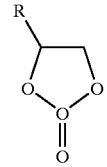
(Ib)

where R is, independently, alkyl; of from 1 to 24 carbon atoms, ethylene glycol, propylene glycol, butyl glycol, pentyl glycol, hexyl glycol, alkyl glycol with 2 to 24 carbon atoms, aromatic, heteroaromatic, or saturated and unsaturated aliphatic cyclic molecule, each with ring sizes of from 3 to 8 carbon atoms and in addition in hetero-cycles N, O, S in place of carbon atoms in any number and combination, alkyl polyol, polyethylene glycol, polypropylene glycol, block and co-polymers of ethylene and propylene glycol and block and copolymers of ethylene glycol, propylene glycol, butyl glycol, pentyl glycol, hexyl glycol, alkyl glycol with 2 to 24 carbon atoms, alkyl triol with 3 to 24 carbon atoms, alkyl tetrol with 4 to 24 carbon atoms, and alkyl pentol with 5 to 24 carbon atoms and alkyl hexol with 6 to 24 carbon atoms, aromatic alcohol, heteroaromatic alcohol, or saturated and unsaturated aliphatic cyclic alcohol, each with ring sizes of from 3 to 8 carbon atoms and in addition in hetero-cycles N, O, S in place of carbon atoms in any number and combination, with from 1 to 6 hydroxyl groups on the cyclic alcohol, and substitution on the ring by $(R_3)_x$ with x being an integer from 0 to 3, where $R_3$ is independently, a $(OH)_y$ substituted alkyl from 1 to 24 carbon atoms where y is an integer from 0 to 6.

The molecular weight of the carbonate is up to approximately 10,000 grams/mol average molecular weight.

Uses

The compounds, products and compositions of the present invention are useful for a multitude of purposes. Such purposes include any known use for the preferred starting material organosilanes of the above-described general formula. In preferred embodiments, the presently described, water-stabilized, organosilane compounds, products, and compositions are suitable to applications such as: 1) treatment of surfaces, including fillers and pigments, 2) additives to coatings such as dyes, 3) as additives to organic monomers (such as acrylics) prior to formation of the respective polymer, 4) addition to the polymer prior to processing into final products, or 5) incorporation into polymer or substrate backbone, such as polyester or concrete.

Therefore, in addition to the utility of prior organosilane quaternary ammonium compounds such as 3-(trimethoxysilyl)propyl-dimethyloctadecyl ammonium chloride as surface bonding antimicrobial agents, numerous other uses of organofunctional silanes are contemplated, such as the use of the compounds, products and compositions of the invention in coating applications which include the treatment of surfaces or particles (pigments or fillers), in primers, in paints, inks, dyes and adhesives, and as reactive intermediates for silicone resin synthesis.

The present invention can be used to prepare, inter alia, agricultural products, cleaning compositions, antimicrobial sponges, antimicrobial bleaching agents, antimicrobial fillers for paints, plastics, or concrete, and to treat concrete structures such as livestock shelters, where microbial infestation is a problem.

In various embodiment, surfaces and substrates treatable with the compounds, products and compositions of the invention solution include, but are not limited to, textiles, carpet, carpet backing, upholstery, clothing, sponges, plastics, metals, surgical dressings, masonry, silica, sand, alumina, aluminum chlorohydrate, titanium dioxide, calcium carbonate, wood, glass beads, containers, tiles, floors, curtains, marine products, tents, backpacks, roofing, siding, fencing, trim, insulation, wall-board, trash receptacles, outdoor gear, water purification systems, and soil. Furthermore, articles treatable with the compounds, products and compositions of the invention include, but are not limited to, air filters and materials used for the manufacture thereof, aquarium filters, buffer pads, fiberfill for upholstery, fiberglass ductboard, underwear and outerwear apparel, polyurethane and polyethylene foam, sand bags, tarpaulins, sails, ropes, shoes, socks, towels, disposal wipes, hosiery and intimate apparel; cosmetics, lotions, creams, ointments, disinfectant sanitizers, wood preservatives, plastics, adhesives, paints, pulp, paper, cooling water, and laundry additives and non-food or food contacting surfaces in general.

For the above described substrates, mixtures and applications, treatment generally involves contacting or mixing the article to be treated with a water-stabilized organosilane solution of the present invention, comprising the organosilane-stabilizer derived compound in an aqueous solution, for a period of time sufficient for permanent bonding of the active organosilane ingredient (or portion thereof) to the article. In alternative embodiments, organosilane-carbonate mixtures according to the invention can be used directly without dilution with water, or, alternatively, dilutions with solvents other than water can be used according to the invention Generally, treatment begins immediately upon contact, but preferably requires from about 15 seconds to about 48 hours. Many examples and guidelines are shown for efficient silane surface treatment and incoporation, for example "Applying A Silane Coupling Agent", page 49, Gelest Catalog, by Gelest, Inc. Tullytown, Pa., 1995. Further general guidelines for application are as follows: For dipping a large object, it is preferred that 1–2 minutes of submersion is allowed in the solution and then the object is permitted to dry or is dried. However, some objects will benefit from very short dipping, mixing or contacting times, for example, fabric may pass through an aqueous bath of the composition at a rate of 40 yards per minute or more. After dipping, excess solution may be gently wiped or rinsed off. Alternatively, the solution may be sprayed on the substrate. Moreover, the composition of the invention may be placed in a high intensity solid mixer and formed into a powder which is then dried. The dried powder may then be used in a sprayer, if desired. In addition, the solutions may be wiped onto the substrate and applied using sponges or cloths, etc. Moreover, the solutions of the present invention can be added to pigments and fillers and stirred therewith for several (2–3) minutes. In addition, the solutions can be added to an emulsion or other existing formulation prior to use. Also, the solutions can be used in addition to, with or as a spray coolant for extruded fibers. However, one of ordinary skill in the art would recognize that numerous other uses and modes of application are readily apparent from the stabilized organosilane compounds, products and compositions of the present invention and would, without undue experimentation, be able to determine effective application methods and treating times for any particular substrate, article, or other application. In addition, the compositions can be used in padding processes as are known in textile mills.

Moreover, after treating a surface or fabric with the compound, product or compositions of the present invention, the surface or fabric may, optionally, be heated to further complete bonding of the compound, product, or composition to the surface or substrate.

The water-stable organosilane compounds, products and compositions of the present invention are, therefore, advantageous in treating a variety of substrates without the use of toxic organic solvents, and provide for the safe, long-term storage of activated organosilanol compound which can be used without further preparation. Moreover, the stabilization scheme described herein does not interfere with the binding of the organosilane (or at least the core, operative portion thereof) to the substrate. In addition, the present invention provides a generally applicable scheme for solvating some water insoluble organosilanes.

Also apparent will be those applications where organosilanes $R_nSiX_{4-n}$ are prepared, dissolved, stored, applied, and in any way used in water. In addition, also apparent will be those applications of organosilanes $R_nSiX_{4-n}$, in other solvents or mixed in other media (solids, polymer mixes, fillers, pigments, powders, dyes or emulsions) where exposure to water occurs but could be detrimental due to undesired or untimely self-condensation of the silanol.

Moreover, the stabilizing compounds and methods could be used in addition to or in conjunction with various art-known stabilization methods for organosilanes, such as the use of ionic or non-ionic surfactants and detergents.

In addition, it is believed that the compounds, products and compositions of the present invention lead to improved wetting and/or coating because the partially hydrolyzed stabilizer/organosilane complex is dense in hydroxyl groups, thus providing for increased hydrogen-bonding to surface OH groups.

Moreover, the present compounds, products and compositions can be used in the incorporation of an organosilane antimicrobial agent in most textile goods (woven and non-woven) and yarns (synthetic and natural). The process provides articles that are durable and the process itself is effective and does not require additional manufacturing steps or increase manufacturing cost.

Further, as is well known in the art, certain classes of organosilanes have properties which can repel water and other liquids. Accordingly, one embodiment of the subject invention is directed toward a method of treating a substrate to render the substrate resistant to stains.

Incorporating the compounds, products and compositions of the present invention during the dye process yields a textile material with a built-in antimicrobial activity or other desired property with the organosilane characteristics. The incorporation process 1) does not add any additional step in the manufacturing process and does not require any equipment modification; and 2) is believed not to lose its antimicrobial characteristics and its effectiveness during further production of the textile goods. By incorporating the water-stable compounds, products and compositions of the present invention during the dye process, not only would the organosilane antimicrobial agent remain unaffected by the dying agent, but the end-product textile goods would also exhibit excellent dyeing properties.

The water-stabilized organosilane compounds, products and compositions of the present invention are useful for a number of applications where the previous instability, insolubility prevented or, at least, hindered or restricted use of some organosilane agents. For example:

Treating food crops (e.g., perishables such as vegetables, fruits, or grains) after removal (pickled/harvested) with the compounds, products and compositions of the present invention imparts antimicrobial protection to the outer surface of the food crop. It is believed that such protection occurs without diff-using, migrating or leaching the antimicrobial agent from the bonded antimicrobial coating of the food item, and provides prolonged, safe and non-toxic antimicrobial protection. The method involves treating fruits and vegetables in the rinse cycle, during or after the normal cleaning/water spraying or during or after blanching. Thorough cleaning of fruits and vegetables at the processing plant is preferred for initially removing microorganisms. As one of ordinary skill in the art would recognize, machines are used initially to remove soil, chemicals used in growing, spoilage bacteria, and other foreign materials. These machines also use high velocity water sprays to clean the products. After the cleaning, raw foods or other crop materials are prepared for further processing such blanching (i.e., the food is immersed in water at 190 to 210 degrees F. or exposed to steam).

Microorganisms are controlled by the production plant up until the fruit or vegetable is removed. But once it is removed, organisms such as yeast, mold, and bacteria, begin to multiply, causing the food to loose flavor and change in color and texture. To keep the food from spoiling, a number of methods have been employed, such as refrigerators, to slow down the microorganisms and delay deterioration. Unfortunately, such known methods will preserve raw foods for few weeks at the most. The compounds, products and compositions of the present invention can preserve these items for extended periods. For instance, the compositions, products, or compounds may be added to an existing water line feeding the sprayers for the foods, where such sprayers are used. Otherwise, a simple dipping process may be used, where the dipping requires only a few seconds to impart antimicrobial protection. Low concentrations of 0.1 to 1% aqueous solution (0.1 to 1% by volume) of the compositions provide satisfactory results. In addition, it is believed that the presently described method can also control pathogens on poultry carcasses and in other susceptible meat and fish.

Treating baby milk/juice bottles, nipples, pacifiers and toys with the compounds, products and compositions of the present invention in the factory or leachinig the agent from the bonded surface, can provide prolonged and safe/non-toxic antimicrobial protection. Treating such articles also eliminates odors caused by microbial contamination. A dipping method as described above may be used to treat these articles.

To date, parents have used soaps, detergents, and surface cleaners to alleviate the problems of contamination of these articles. However, these and other similar treatments have, for the most part, been inadequate and required repeated treatment. In addition, these treatments have been found to be limited in their ability to offer broad spectrum control of microorganisms. Therefore, the present compounds, products and compositions can be used to treat these articles to prevent microbial growth and contamination by coating an effective amount of the products and compounds of the invention thereon. The articles employed can be coated by allowing for 1 to 2 minutes submersion (e.g., by dipping), and thereafter, the treated surface is allowed to dry at room temperature. The article is then rinsed of any excess antimicrobial agent. Thorough cleaning and sterilization is a preferred step in removing the microorganisms on the surface of the article prior to "coating" the said articles. In addition, concentrations of 10% or less by weight of the compounds, products and compositions of the invention in water are used for long lasting protection.

Treating surgical gloves with the compounds, products and compositions of the present invention before or during a surgical procedure can kill microorganisms on contact. It is believed that the treated gloves do not diffuse or leach the antimicrobial agent from the glove surface and provide prolonged antimicrobial activity with safe and non-toxic antimicrobial protection. Surgical gloves are treated, preferably, by submerging in the solution of Example I, diluted to 1% W/V for at least 30 seconds. This method will permit doctors to use and, if necessary, re-use the same gloves (even without removing them) without undue fear of contamination. Treating polymers and other materials such as concrete by incorporation into the bulk material protects from deterioration, odor build-up and potentially harmful contamination of the surface. Incorporation of a sun protection into polymers and/or application of sun protection to the surface extends the life of the product and reduces damage to products and skin.

Moreover, one of ordinary skill in the art would be able to implement numerous other end uses based upon the disclosure of the compounds, products and compositions of the present invention. Not all uses require aqueous solutions and some require non-aqueous environments, both applications are part of the invention. Furthermore antimicrobial properties of the silane compounds according to the invention is only one of many possible properties. Mixtures of silanes according to the invention often provide additional benefits.

For instance, the following uses, applications and substrates, are contemplated:

1. Concrete, Concrete Water Conduits, Storm and Sewer Pipes treated with the compounds, products and compositions of the present invention. Agents to kill microorganism on contact and provide prolonged antimicrobial protection to prevent deterioration of the concrete and its coatings.
2. Tooth Brushes, Combs, Hair Brushes, Dentures and Retainers
3. Spa and Pool Filters meeting stringent requirements that no other antimicrobial agent can meet and protection for Air Filtration such as air conditioning filters, HVAC applications and cabin air
4. Marble Slabs (building facia, tombs, floors) treated with the compounds, products and compositions of the present invention
5. Rubbing Alcohol
6. Statues and exposed art work
7. HDP, high density polyester fabric plastic covers for dump sites, water reservoirs and generally for soil protection
8. Liquid Additive (as flower water preservative for potted plants and cut flowers)
9. Silicone and Teflon coated Fiberglass with antimicrobial protection including acrylic backing wall covering
10. Dryvitt and Stucco finish
11. Waterproofing treated with the compounds, products and compositions of the present invention
12. A method of treating blended cotton before or after picking machines make the cotton into rolls or laps
13. Food packaging and containers
14. Bio-films and adhesives (tapes and silicone wafers)
15. Single Ply Roofing and Roof shingles
16. Fiberglass reinforcement product The preferred embodiments of the above-described water-stabilized antimicrobial compounds, products, compositions, and methods are set forth in the following examples. Other features of the invention will become apparent from the following examples, which are for illustrative purposes only and are not intended as a limitation upon the present invention.

The silane in the following examples is Dow Corning 5772 or a silane of similar composition as Dow Corning 5772. Both are collectively referred to as silane concentrate. A solution or mixture is considered stable if an aqueous solution can be produced and remain without precipitation of the silane for a longer time than would be expected for the non-stabilized silane. If the silane itself is insoluble in water then the formation of an aqueous solution is a benefit within hte scope of the invention.

EXAMPLE 1

Water dilutions of a mixture containing 20.049 g silane concentrate and 20.788 g ethylene carbonate have been stable at 25.9 weight % mixture in water. At 41.4 weight % the water diluted mixture appeared unstable.

The following table lists examples of mixtures and their stability. The entries are in weight percent of total mixture. Concentrated solutions were prepared and then diluted with water accordingly.

A) 24.694 g silane concentrate, 11.596 g glycol ether DB, 13.593 g propylene carbonate.

B) 25.028 g silane concentrate, 5.895 g glycol ether DB, 19.379 g propylene carbonate.

| # | concentrate | DI Water | Stable (Y/N) |
|---|---|---|---|
| A | 1.6 | 98.4 | y |
| A | 7.4 | 92.6 | y |
| A | 14.4 | 85.6 | y |
| A | 28.0 | 72.0 | n |
| A | 41.9 | 58.1 | y |
| A | 55.3 | 44.7 | y |
| B | 1.4 | 98.6 | y |
| B | 7.1 | 92.9 | y |
| B | 13.7 | 86.3 | y |
| B | 26.6 | 73.4 | n |
| B | 42.0 | 58.0 | y |
| B | 54.7 | 45.3 | y |

EXAMPLE 2

The following table lists examples of mixtures and their stability. The entries are in weight percent of total mixture. A solution 50 weight percent silane concentrate and 50 weight percent propylene carbonate was prepared and then diluted with water according to the table.

| concentrate | DI Water | Stable (Y/N) |
|---|---|---|
| 7.5 | 92.5 | y |
| 14.1 | 85.9 | y |
| 28.5 | 71.5 | n |
| 42.0 | 58.0 | y |
| 54.9 | 45.1 | y |

EXAMPLE 3

In a flask were heated and stirred 54.109 g dimethyl octadecyl amine and 53.871 g 3-chloropropyltrimethoxysilane and 14.960 g propylene carbonate. The temperature was held at 130 to 135° C., when the mixture began to darken, the temperature was reduced to 125° C. After 21 hours, titration of the mixture revealed an amine content of 1.3% and an ammonium content of 72.0%. The product was a light brown, soft solid when at room temperature.

The reaction product of the previous example was dissolved in water, to prepare stable silane water mixtures.

| # | concentrate | DI Water | Stable (Y/N) |
|---|---|---|---|
| 1 | 2.0 | 98.0 | y |
| 2 | 6.8 | 93.2 | y |
| 3 | 14.5 | 85.5 | y |
| 4 | 22.2 | 77.8 | n |
| 5 | 28.7 | 71.3 | n |
| 6 | 35.3 | 64.7 | n |

EXAMPLE 4

Sample 2 of the previous example was after 35 days diluted further with 4 parts water and applied to white textile fabric. After drying, the fabric was hand washed in running water 20 times. The sample was again allowed to dry and then tested according to Dow Corning Corporate Test Method 0923. In this test method the fabric sample is placed together with an inoculated nutrient solution into an erlenmeyer flask. For this experiment the procedure was slightly modified, the mixture was shaken for 24 hours instead of 1 hour and the organism used was aspergillus niger instead of klebsiella pneumoniae. Percent reduction is determined by counting the organisms at zero time and at the end of the experiment. The percent reduction found in this example was 99.98%.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with the true scope and spirit of the invention being indicated by the claims.

It should be understood that the examples and embodiments described herein are for illustrative purposes only and that various modifications or changes in light thereof will be suggested to persons skilled in the art and are to be included within the spirit and purview of this application and the scope of the claims.

What is claimed is:

1. A composition comprising a mixture of:
   a) an antimicrobial organosilane of the formula $R_nSiX_{4-n}$, wherein n is an integer of from 0 to 3; and R is, independently, a nonhydrolizable organic group; and each X is, independently, a hydrolyzable group; with
   b) an organic carbonate.

2. The composition of claim 1, wherein n is an integer from 0 to 2; each R of the organosilane formula is, independently, alkyl, alkyl alcohol, or aromatic; each X is, independently, hydroxy, alkoxy, halogen, acetyl, acetoxy, acyl, acyloxy, a hydroxylated solid or liquid polymeric moiety, polyglycol or polyalkylether; and said organic carbonate is of the formula:

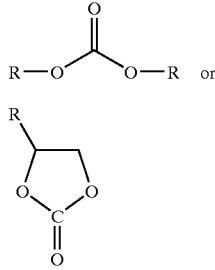

(Ia) or (Ib)

wherein R of the carbonate formula is, independently, alkyl, glycol, alkyl glycol, a cyclic molecule, or a heterocyclic molecule; alkyl alcohol, polyglycol, alkyl glycol, cyclic alcohol, heterocyclic alcohol, or polyalkyl ether; optionally said cyclic alcohol or heterocyclic alcohol is substituted with an alkyl or an alkyl alcohol.

3. The composition of claim 1, wherein the organosilane is of the formula II, III, IV, or V:

$$(R_1)_3SiR_2N^+(R_3)(R_4)(R_5)Y^- \quad (II)$$

$$(R_1)_3SiR_2N(R_3)(R_4) \quad (III)$$

$$(R_1)_3SiR_2R_{35} \quad (IV)$$

$$(R_1)_2Si(R_{36})(R_{37}) \quad (V)$$

wherein
each $R_1$ is, independently, halogen or $R_6O$; where $R_6$ is selected from the group consisting of the following:
H, alkyl, acetyl, acetoxy, acyl, acyloxy, glycol, polyglycol, alkyl glycol, alkyl polyglycol, a monoester formed by linking a carbonic acid of from 1 to 24 carbons with glycol or polyglycol, phenolics substituted with an alkyl of from about 1 to 24 carbons and their ethers and sorbitan esters and their ethers and polyalkyl ether;
$R_{35}$ is $R_6$, H, halogen, $NH_2(CH_2)_2NHR_2$, $NH_2R_2$, $C_3H_5O_2R_2$, $C_4H_5O_2R_2$, $NaO(CH_3O)P(O)R_2$, or $ClCH_2C_6H_4R_2$;
$R_{36}$ and $R_{37}$ are, independently, $R_{35}$, halogen, H, alkyl of from 1 to about 4 carbon atoms, isobutyl, phenyl, or n-octyl;
$R_2$ is $R_6$, benzyl, vinyl or alkyl;
$R_3$ and $R_4$ are, independently, $R_{35}$ alkyl alcohol, alkoxy, alkyl or a cyclic molecule; or
$R_3$ and $R_4$ can, together, form a morpholine, a cyclic molecule, or a heterocyclic molecule;
$R_5$ is alkyl alcohol, $R_{35}$, $CH_2C_6H_5$, polyglycol, alkyl, alkoxy, perfluoroalkyl, pefluoroalkylsulfonate, or perfluoroalkylcarboxylate; and
$Y^-$ is a suitable anionic moiety to form the salt of the compound of formula I, II, III or IV.

4. A water stable composition, comprising the composition of claim 1 and water.

5. The composition of claim 1, wherein the organosilane is 3-(trimethoxysilyl)propyldimethyloctadecyl ammonium chloride.

6. A composition for treating a substrate, comprising a carrier and an effective amount of the composition of claim 1.

7. The composition of claim 6, wherein the carrier is other than water.

8. The composition of claim 1, wherein the organosilane is 3-(trimethoxysilyl)propyldimethyloctadecyl ammonium chloride, 3-(trimethoxysilyl)propylmethyldi(decyl) ammonium chloride, 3-chloropropyltrimethylsilane, 3-chloropropyltrimethoxysilane, octadecyltrimethoxysilane, or perfluorooctyltriethoxysilane.

9. The composition of claim 1, wherein the organosilane is $(CH_3O)_3Si(CH_2)_3N^+(CH_3)_2C_{18}H_{37}Cl^-$, $(CH_3O)_3Si(CH_2)_3 N^+(CH_3)_2C_{18}H_{37}Br^-$, $(CH_3O)_3Si(CH_2)_3N^+(C_{10}H_{21})_2CH_3Cl^-$, $(CH_3O)_3Si(CH_2)_3 N^+(C_{10}H_{21})_2CH_3Br^-$, $(CH_3O)_3Si(CH_2)_3N^+(CH_3)_3Cl^-$, $(CH_3O)_3Si(CH_2)_3N^+(CH_3)_2C_8H_{17}Cl^-$, $(CH_3O)_3Si(CH_2)_3N^+(CH_3)_2C_{10}H_{21}Cl^-$, $(CH_3O)_3Si(CH_2)_3 N^+(CH_3)_2C_{12}H_{25}Cl^-$, $(CH_3O)_3Si(CH_2)_3N^+(CH_3)_2C_{14}H_{29}Cl_-$, $(CH_3O)_3Si(CH_2)_3 N^+(CH_3)_2C_{16}H_{33}Cl^-$, $(CH_3O)_3Si(CH_2)_3N^+(CH_3)_2C_{20}H_{41}Cl^-$, $(CH_3O)_3Si(CH_2)_3 N^+(C_4H_9)_3Cl^-$, $(CH_3O)_3Si(CH_2)_3N^+(C_2H_5)_3C^-$, $(CH_3CH_2O)_3Si(CH_2)_3 N^+(CH_3)_2C_{18}H_{27}Cl^-$, $(CH_3O)_3Si(CH_2)_3NHC(O)(CF_2)_6CF_3$, $(CH_3O)_3Si(CH_2)_3 NHC(O)(CF_2)_8CF_3$, $(CH_3O)_3Si(CH_2)_3NHC(O)(CF_2)_{10}CF_3$, $(CH_3O)_3Si(CH_2)_3 NHC(O)(CF_2)_{12}CF_3$, (CH₃O)Si(CH₂)₃NHC(O)(CF₂)₁₄CF₃, (CH₃O)₃Si(CH₂)₃NHC(O)(CF₂)₁₆CF₃,
(CH₃O)₃Si(CH₂)₃NHSO₂(CF₂)₇CF₃,
(CH₃O)₃Si(CH₂)₃N⁺(CH₃)₂(CH₂)₃NHC(O)(CH₂)₆CH₃,
(CH₃O)₃Si(CH₂)₃N⁺,(CH₃)₂(CH₂)₃NHC(O)(CH₂)₈CH₃,
(CH₃O)₃Si(CH₂)₃N⁺(CH₃)₂(CH₂)₃NHC(O)(CH₂)₁₀CH₃,
(CH₃O)₃Si(CH₂)₃N⁺(CH₃)₂(CH₂)₃NHC(O)(CH₂)₁₂CH₃,
(CH₃O)₃Si(CH₂)₃N⁺(CH₃)₂(CH₂)₃NHC(O)(CH₂)₁₄CH₃,
(CH₃O)₃Si(CH₂)₃N⁺(CH₃)₂(CH₂)₃NHC(O)(CH₂)₁₆CH₃,
(CH₃O)₃Si(CH₂)₃N⁺(CH₃)₂(CH₂)(CH₂)₃NHC(O)(CF₂)₆C₃,
(CH₃O)₃Si(CH₂)₃N⁺(CH₃)₂(CH₂)₃NHC(O)(CF₂)₈CF₃,
(CH₃O)₃Si(CH₂)₃N⁺(CH₃)₂(CH₂)₃NHC(O)(CF₂)₁₀CF₃,
(CH₃O)₃Si(CH₂)₃N⁺(CH₃)₂(CH₂)₃NHC(O)(CF₂)₁₂CF₃,
(CH₃O)₃Si(CH₂)₃N⁺(CH₃)₂(CH₂)₃NHS(O)(CF₂)₁₄CF₃,
(CH₃O)₃Si(CH₂)₃N⁺(CH₃)₂(CH₂)₃NHC(O)(CF₂)₁₆CF₃,
(CH₃O)₃Si(CH₂)₃N⁺(CH₃)₂(CH₂)₃NHSO₂(CF₂)₇CF₃,
(CH₃O)₃Si(CH₂)₃N⁺(CH₃)₂(CH₂)₃NHSO₂(CF₂)₉CF₃,
(CH₃O)₃Si(CH₂)₃N⁺(CH₃)₂(CH₂)₃NHSO₂(CF₂)₁₁CF₃,
(CH₃O)₃Si(CH₂)₃N⁺(CH₃)₂(CH₂)₃NHSO₂(CF₂)₁₃CF₃,
(CH₃O)₃Si(CH₂)₃N⁺(CH₃)₂(CH₂)₃NHSO₂(CF₂)₁₅CF₃,
(CH₃O)₃Si(CH₂)₃N⁺(CH₃)₂(CH₂)₃NHSO₂(CF₂)₁₆CF₃,
(CH₃O)₃Si(CH₂)₃NHC₆H₄COOH,
(CH₃O)₃Si(CH₂)₃NHC₆H₄COOCH₃,
(CH₃O)₃Si(CH₂)₃NHC₆H₄COOC₂H₅,
(CH₃O)₃Si(CH₂)₃NHC₆H₄COOC₃H₇,
(CH₃O)₃Si(CH₂)₃NHC₆H₄COOC₄H₉,
(CH₃O)₃Si(CH₂)₃NHC₆H₄COOCH₂C₆H₅,
(CH₃O)₃Si(CH₂)₃NHC₆H₄COOCH₂C₆H₄NH₂,
(CH₃O)₃Si(CH₂)₃NHC₆H₄COOCH₂C₆H₄N(CH₃)₂,
(CH₃O)₃Si(CH₂)₃NHC₆H₄COOCH₂C₆H₄N(CH₂CH₃)₂,
(CH₃O)₃Si(CH₂)₃NHC₆H₄COOCH₂C₆H₄N⁺(CH₃)₃ Y⁻,
(CH₃O)₃Si(CH₂)₃NHC₆H₄COOCH₂C₆H₄N⁺(CH₂CH₃)₃ Y⁻,
(CH₃O)₃Si(CH₂)₃NCH₃C₆H₄COOH,
(CH₃O)₃Si(CH₂)₃NCH₃C₆H₄COOCH₃,
(CH₃O)₃Si(CH₂)₃NCH₃C₆H₄COOC₂H₅,
(CH₃O)₃Si(CH₂)₃NCH₃C₆H₄COOC₃H₇,
(CH₃O)₃Si(CH₂)₃NCH₃C₆H₄COOC₄H₉,
(CH₃O)₃Si(CH₂)₃NCH₃C₆H₄COOCH₂C₆H₅,
(CH₃O)₃Si(CH₂)₃NCH₃C₆H₄COOCH₂C₆H₄NH₂,
(CH₃O)₃Si(CH₂)₃NCH₃C₆H₄COOCH₂C₆H₄N(CH₃)₂,
(CH₃O)₃Si(CH₂)₃NCH₃C₆H₄COOCH₂C₆H₄N(CH₂CH₃)₂,
(CH₃O)₃Si(CH₂)₃NCH₃C₆H₄COOCH₂C₆H₄N⁺(CH₃)₃ Y⁻,
(CH₃O)₃Si(CH₂)₃NCH₃C₆H₄COOCH₂C₆H₄N⁺(CH₂CH₃)₃ Y⁻,
(CH₃O)₃Si(CH₂)₃N⁺(CH₃)₂C₆H₄COOH Y⁻,
(CH₃O)₃Si(CH₂)₃N⁺(CH₃)₂C₆H₄COOCH₃ Y⁻,
(CH₃O)₃Si(CH₂)₃N⁺(CH₃)₂C₆H₄COOC₂H₅ Y⁻,
(CH₃O)₃Si(CH₂)₃N⁺(CH₃)₂C₆H₄COOC₃H₇ Y⁻,
(CH₃O)₃Si(CH₂)₃N⁺(CH₃)₂C₆H₄COOC₄H₉ Y⁻,
(CH₃O)₃Si(CH₂)₃N⁺(CH₃)₂C₆H₄COOCH₂C₆H₅ Y⁻,
(CH₃O)₃Si(CH₂)₃N⁺(CH₃)₂C₆H₄COOCH₂C₆H₄NH₂ Y⁻,
(CH₃O)₃Si(CH₂)₃N⁺(CH₃)₂C₆H₄COOCH₂C₆H₄N(CH₃)₂ Y⁻,
(CH₃O)₃Si(CH₂)₃N⁺(CH₃)₂C₆H₄COOCH₂C₆H₄N(CH₂CH₃)₂ Y⁻,
(CH₃O)₃Si(CH₂)₃N⁺(CH₃)₂C₆H₄COOCH₂C₆H₄N⁺(CH₃)₃ Y⁻Y⁻,
(CH₃O)₃Si(CH₂)₃N⁺(CH₃)₂C₆H₄COOCH₂C₆H₄N⁺(CH₂CH₃)₃ Y⁻Y⁻,
(CH₃O)₃Si(CH₂)₃NC₂H₅C₆H₄COOH,
(CH₃O)₃Si(CH₂)₃NC₂H₅C₆H₄COOCH₃,
(CH₃O)₃Si(CH₂)₃NC₂H₅C₆H₄COOC₄H₉,
(CH₃O)₃Si(CH₂)₃NC₂H₅C₆H₄COOC₃H₇,
(CH₃O)₃Si(CH₂)₃NC₂H₅C₆H₄COOC₄H₉,
(CH₃O)₃Si(CH₂)₃NC₂H₅C₆H₄COOCH₂C₆H₅,
(CH₃O)₃Si(CH₂)₃NC₂H₅C₆H₄COOCH₂C₆H₄NH₂,
(CH₃O)₃Si(CH₂)₃NC₂H₅C₆H₄COOCH₂C₆H₄N(CH₃)₂,
(CH₃O)₃Si(CH₂)₃NC₂H₅C₆H₄COOCH₂C₆H₄N(CH₂CH₃)₂,
(CH₃O)₃Si(CH₂)₃NC₂H₅C₆H₄COOCH₂C₆H₄N⁺(CH₃)₃ Y⁻,
(CH₃O)₃Si(CH₂)₃NC₂H₅C₆H₄COOCH₂C₆H₄N⁺(CH₂CH₃)₃ Y⁻,
(CH₃O)₃Si(CH₂)₃N⁺(C₂H₅)₂C₆H₄COOH Y⁻,
(CH₃O)₃Si(CH₂)₃N⁺(C₂H₅)₂C₆H₄COOCH₃ Y⁻,
(CH₃O)₃Si(CH₂)₃N⁺(C₂H₅)₂C₆H₄COOC₂H₅ Y⁻,
(CH₃O)₃Si(CH₂)₃N⁺(C₂H₅)₂C₆H₄COOC₃H₇ Y⁻,
(CH₃O)₃Si(CH₂)₃N⁺(C₂H₅)₂C₆H₄COOC₄H₉ Y⁻,
(CH₃O)₃Si(CH₂)₃N⁺(C₂H₅)₂C₆H₄COOCH₂C₆H₅ Y⁻,
(CH₃O)₃Si(CH₂)₃N⁺(C₂H₅)₂C₆H₄COOCH₂C₆H₄N₂ Y⁻,
(CH₃O)₃Si(CH₂)₃N⁺(C₂H₅)₂C₆H₄COOCH₂C₆H₄N(CH₃)₂ Y⁻,
(CH₃O)₃Si(CH₂)₃N⁺(C₂H₅)₂C₆H₄COOCH₂C₆H₄N(CH₂CH₃)₂ Y⁻,
(CH₃O)₃Si(CH₂)₃N⁺(C₂H₅)₂C₆H₄COOCH₂C₆H₄N⁺(CH₃)₃ Y⁻Y⁻,
(CH₃O)₃Si(CH₂)₃N⁺(C₂H₅)₂C₆H₄COOCH₂C₆H₄N⁺(CH₂CH₃)₃ Y⁻Y⁻,
(CH₃CH₂O)₃Si(CH₂)₃NHC₆H₄COOH,
(CH₃CH₂O)₃Si(CH₂)₃NHC₆H₄COOCH₃,
(CH₃CH₂O)₃Si(CH₂)₃NHC₆H₄COOC₂H₅,
(CH₃CH₂O)₃Si(CH²)₃NHC₆H₄COOC₃H₇,
(CH₃CH₂O)₃Si(CH₂)₃NHC₆H₄COOC₄H₉,
(CH₃CH₂O)₃Si(CH₂)₃NHC₆H₄COOCH₂C₆H₅,
(CH₃CH₂O)₃Si(CH₂)₃NHC₆H₄COOCH₂C₆H₄NH₂,
(CH₃CH₂O)₃Si(CH₂)₃NHC₆H₄COOCH₂C₆H₄N(CH₃)₂,
(CH₃CH₂O)₃Si(CH₂)₃NHC₆H₄COOCH₂C₆H₄N(CH₂CH₃)₂,
(CH₃CH₂O)₃Si(CH₂)₃NHC₆H₄COOCH₂C₆H₄N⁺(CH₃)₃ Y⁻,
(CH₃CH₂O)₃Si(CH₂)₃NHC₆H₄COOCH₂C₆H₄N⁺(CH₂CH₃)₃ Y⁻,
(CH₃CH₂O)₃Si(CH₂)₃NCH₃C₆H₄COOH,
(CH₃CH₂O)₃Si(CH₂)₃NCH₃C₆H₄COOCH₃,
(CH₃CH₂O)₃Si(CH₂)₃NCH₃C₆H₄COOC₂H₅,
(CH₃CH₂O)₃Si(CH₂)₃NCH₃C₆H₄COOC₃H₇,
(CH₃CH₂O)₃Si(CH₂)₃NCH₃C₆H₄COOC₄H₉,
(CH₃CH₂O)₃Si(CH₂)₃NCH₃C₆H₄COOCH₂C₆H₅,
(CH₃CH₂O)₃Si(CH₂)₃NCH₃C₆H₄COOCH₂C₆H₄NH₂,
(CH₃CH₂O)₃Si(CH₂)₃NCH₃C₆H₄COOCH₂C₆H₄N(CH₃)₂,
(CH₃CH₂O)₃Si(CH₂)₃NCH₃C₆H₄COOCH₂C₆H₄N(CH₂CH₃)₂,
(CH₃CH₂O)₃Si(CH₂)₃NCH₃C₆H₄COOCH₂C₆H₄N⁺(CH₃)₃ Y⁻, $(CH_3CH_2O)_3Si(CH_2)_3NCH_3C_6H_4COOCH_2C_6H_4N^+(CH_2CH_3)_3\ Y^-$,
$(CH_3CH_2O)_3Si(CH_2)_3NCH_3C_6H_4COOCH_2C_6H_4N^+(CH_2CH_3)_3\ Y^-$,
$(CH_3CH_2O)_3Si(CH_2)_3N^+(CH_3)_2C_6H_4COOH\ Y^-$,
$(CH_3CH_2O)_3Si(CH_2)_3N^+(CH_3)_2C_6H_4COOCH_3\ Y^-$,
$(CH_3CH_2O)_3Si(CH_2)_3N^+(CH_3)_2C_6H_4COOC_2H_5\ Y^-$,
$(CH_3CH_2O)_3Si(CH_2)_3N^+(CH_3)_2C_6H_4COOC_3H_7\ Y^-$,
$(CH_3CH_2O)_3Si(CH_2)_3N^+(CH_3)_2C_6H_4COOC_4H_9\ Y^-$,
$(CH_3CH_2O)_3Si(CH_2)_3N^+(CH_3)_2C_6H_4COOCH_2C_6H_5\ Y^-$,
$(CH_3CH_2O)_3Si(CH_2)_3N^+(CH_3)_2C_6H_4COOCH_2C_6H_4NH_2\ Y^-$,
$(CH_3CH_2O)_3Si(CH_2)_3N^+(CH_3)_2C_6H_4COOCH_2C_6H_4N(CH_3)_2\ Y^-$,
$(CH_3CH_2O)_3Si(CH_2)_3N^+(CH_3)_2C_6H_4COOCH_2C_6H_4N(CH_2CH_3)_2\ Y^-$,
$(CH_3CH_2O)_3Si(CH_2)_3N^+(CH_3)_2C_6H_4COOCH_2C_6H_4N^+(CH_3)_3\ Y^-Y^-$,
$(CH_3CH_2O)_3Si(CH_2)_3N^+(CH_3)_2C_6H_4COOCH_2C_6H_4N^+(CH_2CH_3)_3\ Y^-Y^-$,
$(CH_3CH_2O)_3Si(CH_2)_3NC_2H_5C_6H_4COOH$,
$(CH_3CH_2O)_3Si(CH_2)_3NC_2H_5C_6H_4COOCH_3$,
$(CH_3CH_2O)_3Si(CH_2)_3NC_2H_5C_6H_4COOC_2H_5$,
$(CH_3CH_2O)_3Si(CH_2)_3NC_2H_5C_6H_4COOC_3H_7$,
$(CH_3CH_2O)_3Si(CH_2)_3NC_2H_5C_6H_4COOC_4H_9$,
$(CH_3CH_2O)_3Si(CH_2)_3NC_2H_5C_6H_4COOCH_2C_6H_5$,
$(CH_3CH_2O)_3Si(CH_2)_3NC_2H_5C_6H_4COOCH_2C_6H_4NH_2$,
$(CH_3CH_2O)_3Si(CH_2)_3NC_2H_5C_6H_4COOCH_2C_6H_4N(CH_3)_2$,
$(CH_3CH_2O)_3Si(CH_2)_3NC_2H_5C_6H_4COOCH_2C_6H_4N(CH_2CH_3)_2$,
$(CH_3CH_2O)_3Si(CH_2)_3NC_2H_5C_6H_4COOCH_2C_6H_4N^+(CH_3)_3\ Y^-$,
$(CH_3CH_2O)_3Si(CH_2)_3NC_2H_5C_6H_4COOCH_2C_6H_4N^+(CH_2CH_3)_3\ Y^-$,
$(CH_3CH_2O)_3Si(CH_2)_3N^+(C_2H_5)_2C_6H_4COOH\ Y^-$,
$(CH_3CH_2O)_3Si(CH_2)_3N^+(C_2H_5)_2C_6H_4COOCH_3\ Y^-$,
$(CH_3CH_2O)_3Si(CH_2)_3N^+(C_2H_5)_2C_6H_4COOC_2H_5\ Y^-$,
$(CH_3CH_2O)_3Si(CH_2)_3N^+(C_2H_5)_2C_6H_4COOC_3H_7\ Y^-$,
$(CH_3CH_2O)_3Si(CH_2)_3N^+(C_2H_5)_2C_6H_4COOC_4H_9\ Y^-$,
$(CH_3CH_2O)_3Si(CH_2)_3N^+(C_2H_5)H_2C_6H_5\ Y^-$,
$(CH_3CH_2O)_3Si(CH_2)_3N^+(C_2H_5)_2C_6H_4COOCH_2C_6H_4NH_2\ Y^-$,
$(CH_3CH_2O)_3Si(CH_2)_3N^+(C_2H_5)_2C_6H_4COOCH_2C_6H_4N(CH_3)_2\ Y^-$,
$(CH_3CH_2O)_3Si(CH_2)_3N^+(C_2H_5)_2C_6H_4COOCH_2C_6H_4N(CH_3)_2\ Y^-$,
$(CH_3CH_2O)_3Si(CH_2)_3N^+(C_2H_5)_2C_6H_4COOCH_2C_6H_4N(CH_2CH_3)_2\ Y^-$,
$(CH_3CH_2O)_3Si(CH_2)_3N^+(C_2H_5)_2C_6H_4COOCH_2C_6H_4N^+((CH_3)_3\ Y^-Y^-$, or
$(CH_3CH_2O)_3Si(CH_2)_3N^+(C_2H_5)_2C_6H_4COOCH_2C_6H_4N^+(CH_2CH_3)_3\ Y^-Y^-$.

10. The composition of claim 1 formed from mixing an antimicrobial organosilane of the formula II, III, IV, or V:

$$(R_1)_3SiR_2N^+(R_3)(R_4)(R_5)Y^- \quad (II)$$

$$(R_1)_3SiR_2N(R_3)(R_4) \quad (III)$$

$$(R_1)_3SiR_2R_{35} \quad (IV)$$

$$(R_1)_2Si(R_{36})(R_{37}) \quad (V)$$

wherein
each $R_1$ is, independently, halogen or $R_6O$, where $R_6$ is selected from the group consisting of the following:
H, alkyl, acetyl, acetoxy, acyl, acyloxy, glycol, polyglycol, alkyl glycol, alkyl polyglycol, a monoester formed by linking a carbonic acid of from 1 to 24 carbons with glycol or polyglycol; phenolics substituted with an alkyl of from about 1 to 24 carbons and their ethers, and sorbitan esters and their ethers, and polyalkyl ether
$R_{35}$ is $R_6$, H, halogen, $NH_2(CH_2)_2NHR_2$, $NH_2R_2$, $C_3H_5O_2R_2$, $C_4H_5O_2R_2$, $NaO(CH_3O)P(O)R_2$, or $ClCH_2C_6H_4R_2$;
$R_{36}$ and $R_{37}$ are, independently, $R_{35}$, halogen, H, alkyl of from 1 to about 8 carbon atoms, acrylic, vinyl, acetylenic, benzyl, styryl, propinyl, isobutyl, phenyl, or n-octyl;
$R_2$ is benzyl, vinyl or alkyl;
$R_3$ and $R_4$ are, independently, lower alkyl alcohol, lower alkoxy of from 1 to 4 carbon atoms, alkyl of from 1 to about 24 carbon atoms; or $R_3$ and $R_4$ can, together, form a morpholine or cyclic molecule or heterocyclic molecule;
$R_5$ is lower alkyl alcohol, $CH_2C_6H_5$, polyglycol, alkyl, alkoxy, perfluoroalkyl, pefluoroalkylsulfonate, or perfluoroalkylcarboxylate; and
$Y^-$ is a suitable anionic moiety to form the salt of the compound of formula I, II, III or IV,
with an organic carbonate.

11. The composition of claim 10 which is an aqueous composition.

12. A method for making an organosilane of the formula $R_nSiX_{4-n}$ where n is an integer of from 0–3, preferably 0–2; each R is, independently, a nonhydrolizable organic group; and each X is, independently, a hydrolyzable group; which comprises mixing the organosilane synthesis starting materials in an aqueous solution in the presence of an organic carbonate.

13. A water-stable composition comprising from about 0.001% to about 26% antimicrobial organosilane and from about 0.001% to about 26% ethylene carbonate and from about 99.9% to about 48% water.

14. A water-stable composition comprising from about 1.6% to about 56% of an antimicrobial organosilane solution and from about 44% to about 99% water, wherein said organosilane solution comprises about 49% silane concentrate, about 32% glycol ether DB, and about 37% propylene carbonate.

15. A water-stable composition comprising from about 1% to about 55% of an antimicrobial organosilane solution and from about 45% to about 99% water, wherein said organosilane solution comprises about 50% silane concentrate, about 12% glycol ether DB, and about 38% propylene carbonate.

16. A composition comprising from about 7% to about 55% of an antimicrobial organosilane solution and from about 45% to about 93% water, wherein said organosilane solution comprises about 0% to about 50% silane concentrate and about 0% to about 50% propylene carbonate.

17. A composition comprising antimicrobial organosilane, propylene carbonate, and water.

18. A composition comprising antimicrobial organosilane, ethylene carbonate, and water.

19. A method for making an organosilane of the formula $R_nSiX_{4-n}$ where n is an integer of from 0–3, preferably 0–2;

each R is, independently, a nonhydrolizable organic group; and each X is, independantly, a hydrolyzable group; which comprises mixing the organosilane synthesis starting materials in the presence of an organic carbonate solvent.

20. The method according to claim 19 wherein the organosilane starting materials comprise a silane component and a amine.

21. The method according to claim 20 wherein the silane component is 3-chloropropyltrimethoxysilane and the amine dimethyl octadecyl amine.

22. The method according to claim 19 wherein didecyl-N-methyl-3-(trimethoxysilyl)propanaminium chloride is synthesized.

* * * * *